United States Patent [19]
Nakagawa et al.

[11] Patent Number: 4,782,155
[45] Date of Patent: Nov. 1, 1988

[54] CEPHALOSPORIN DERIVATIVES, PROCESSES FOR THEIR PREPARATION AND ANTIBACTERIAL AGENTS

[75] Inventors: Susumu Nakagawa; Norikazu Otake; Ryosuke Ushijima, all of Okazaki, Japan

[73] Assignee: Banyu Pharmaceutical Co., Ltd., Tokyo, Japan

[21] Appl. No.: 29,903

[22] Filed: Mar. 25, 1987

Related U.S. Application Data

[63] Continuation-in-part of Ser. No. 911,780, Sep. 26, 1986.

[30] Foreign Application Priority Data

Mar. 19, 1986 [JP] Japan .................................. 61-59368
Nov. 14, 1986 [JP] Japan .................................. 61-269804

[51] Int. Cl.$^4$ ............................................ C07D 217/02
[52] U.S. Cl. .......................................... 546/47; 544/47; 546/139
[58] Field of Search ............................. 546/147, 139

[56] References Cited

FOREIGN PATENT DOCUMENTS 46-39700 11/1971 Japan .................................. 546/147

OTHER PUBLICATIONS

Partanen, "Chemical Abstracts," vol. 87, 1977, Col. 128178c.
Fourneau, et al., "Chemical Abstracts", vol. 71, 1969, Col. 81108g.
Lucas, *Organic Chemistry*, Sec. Ed., 1953, Amer. Book Co., N.Y., pp. 137–143, 158–161 and 512–513.
Nakagawa et al., ICAAC Abstract, Sep. 1985.

*Primary Examiner*—Richard L. Raymond
*Assistant Examiner*—James H. Turnipseed
*Attorney, Agent, or Firm*—Oblon, Fisher, Spivak, McClelland & Maier

[57] ABSTRACT

The compound having the formula:

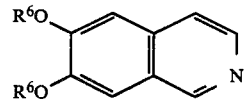

wherein $R^6$ is a hydrogen atom or an alkanoyl group, or a salt thereof and a process thereof.

4 Claims, No Drawings

CEPHALOSPORIN DERIVATIVES, PROCESSES FOR THEIR PREPARATION AND ANTIBACTERIAL AGENTS

This application is continuation-in-part of U.S. patent application Ser. No. 911,780 filed Sept. 26, 1986.

BACKGROUND OF THE INVENTION

1. Field of the Invention

The present invention relates to novel cephalosporin derivatives, processes for their preparation and antibacterial agents containing them as active ingredients. The present invention also relates to novel isoquinoline derivatives which are intermediates of said cephalosporin derivatives and a process for their preparation.

2. Description of the Prior Art

A number of cephalosporin compounds have been synthesized which have a 2-(2-aminothiazol-4-yl)-2-substituted oxyiminoacetamido group as a side chain at the 7-position of the cephem nucleus. As publications which disclose such compounds, Japanese Unexamined Patent Publication Nos. 102293/1977, 116492/1977, 137988/1978, 9296/1979, 154786/1979, 157596/1979, 154980/1980, 6187/1981, 59895/1982, 99592/1982, 92394/1982 and 174387/1983, may be mentioned. It is suggested that such compounds exhibit activities against Gram-positive bacteria and cephalosporin resistant Gram-negative bacteria including *Pseudomonas aeruginosa*, and they have excellent antibacterial activities and a broad antibacterial spectrum. However, few of them are substantially active against glucose non-fermentative Gram-negative rods, such as *Pseudomonas aeruginosa, Pseudomonas cepacia, Pseudomonas maltophilia* and *Acinetobacter calcoaceticus*.

Further, Japanese Unexamined Patent Publication Nos. 57386/1983 and 130294/1989 disclose compounds having an isoquinoliniomethyl group at the 3-position of the cephem nucleus. Japanese Unexamined Patent Publication No. 57386/1983 discloses unsubstituted and mono-substituted isoquinoliniomethyl groups. A number of substituents are mentioned. However, so long as a hydroxyl group is concerned, only a 5-OH derivative and a 8-OH derivative have been synthesized. Japanese Unexamined Patent Publication No. 130294/1984 discloses that the isoquinoline nucleus may have a number of substituents. However, only the 5-OH derivative has been practically synthesized. With respect to the hydroxyl group-substituted compounds, these prior art references give merely general statements, and no data on the antibacterial activities are given. Further, there is no disclosure which teaches that the isoquinoline ring may have two hydroxyl groups, and there is no suggestion at all about 6,7-dihydroxy derivatives having adjacent hydroxyl groups.

Since β-lactam antibiotics exhibit selective toxicity only against bacteria and present no substantial effects against animal cells, they have been widely used as antibiotics having no substantial side effects for the treatment of infectious diseases caused by bacteria, and thus they are highly useful drugs.

However, in recent years, glucose non-fermentative Gram-negative rods, particularly *Pseudomonas aeruginosa* have been frequently isolated as causative organisms of refractory infections from immuno-compromised patients, which has posed a serious problem. Therefore, it is desired and beneficial as well to provide antimicrobial agents with improved activity against such bacteria.

Further, as the starting compound of the formula VIII given hereinafter, there may be mentioned 6,7-dibenzyloxyisoquinoline and 6,7-dimethoxyisoquinoline. A process for preparing 6,7-dimethoxyisoquinoline is disclosed in Journal of the American Chemical Society, Vol. 79, p 3773 (1957), and J. Chem. Soc. Perkin Trans. I, p 2185 (1974) and p 2190 (1974). However, the isoquinoline derivatives of the formula III and VII given hereinafter, which are the intermediates of the cephalosporin derivatives of the present invention, are new compounds not disclosed in any literature.

SUMMARY OF THE INVENTION

It is an object of the present invention to provide novel cephalosporin derivatives having excellent antibacterial activities.

As a result of an extensive research, it has been found that novel cephalosporin derivatives having a 6,7-dihydroxyisoquinoliniomethyl group or a 6,7-diacetoxyisoquinoliniomethyl group at the 3-position and a 2-(2-aminothiazol-4-yl)-2-substituted oxyiminoacetamido group at the 7-position, have strong antibacterial activities against Gram-negative bacteria particularly glucose non-fermentative Gram-negative rods, such as *Pseudomonas aeruginosa, Pseudomonas cepacia, Pseudomonas maltophilia*, and *Acinetobacter calcoaceticus* as compared with a compound having a non-substituted isoquinoline nucleus and with a monohydroxy compound, and they have excellent stability against β-lactamase and a low β-lactamase inducibility. The present invention has been accomplished on the basis of these discoveries.

Namely, the present invention has been accomplished on the basis of the discoveries such that the compounds of the present invention having hydroxyl groups or acetoxy groups at the 6- and 7-positions of the isoquinoline nucleus in the isoquinoliniomethyl group at the 3-position of the cephem nucleus are new compounds not disclosed in any literature, and that they have unexpectedly high antibacterial activities particularly against resistant Gram-negative bacteria as compared with compounds wherein the isoquinoline nucleus is unsubstituted or monohydroxy substituted (the compounds of Reference Examples 1 and 2 correspond to compounds of Examples 57 and 36 of Japanese Unexamined Patent Publication No. 130294/1984 respectively; the compounds of Reference Examples 2 and 3 correspond to compounds of Examples 7 and 6 of Japanese Unexamined Patent Publication No. 57386/1983 respectively) and they have excellent stability against β-lactamase.

Further, the starting materials of isoquinoline derivatives are new compounds not disclosed in any literature, and useful as the intermediates for the cephalosporin derivatives which have improved antibacterial activities.

The present invention provides a compound having the formula:

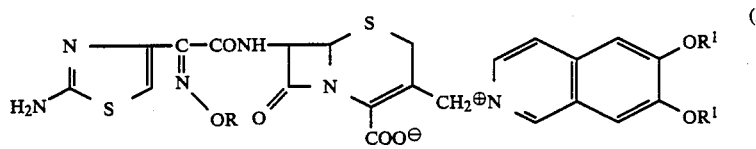

wherein R is a straight chain, branched chain or cyclic lower alkyl, lower alkenyl or lower alkynyl group which may be substituted by a carboxyl group, and $R^1$ is a hydrogen atom or an acetyl group; or a pharmaceutically acceptable salt, physiologically hydrolyzable ester or solvate thereof.

Further, the present invention provides a process for preparing the compound of the formula I, which comprises reacting a compound having the formula:

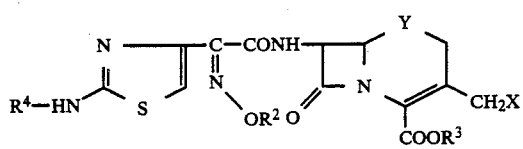

wherein $R^2$ is a straight chain, branched chain or cyclic lower alkyl, lower alkenyl or lower alkynyl group which may be substituted by a protected carboxyl group, $R^3$ is a hydrogen atom or a carboxyl-protecting group, $R^4$ is a hydrogen atom or an amino-protecting group, X is a leaving group, and Y is S or SO, or a salt thereof, with an amine having the formula:

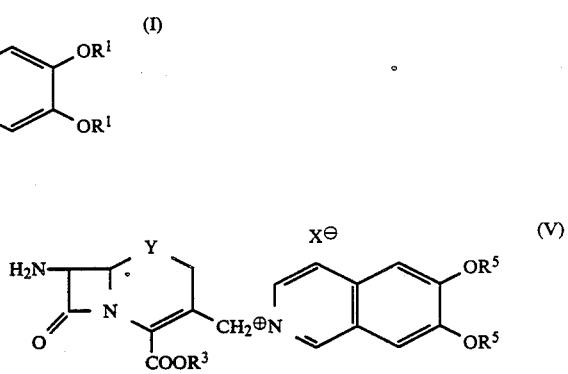

wherein $R^3$ is a hydrogen atom or a carboxyl-protecting group, $R^5$ is a hydrogen atom or a hydroxyl-protecting group, $X^\ominus$ is an anion, and Y is S or SO, or a salt thereof, with a reactive derivative of a carboxylic acid having the formula:

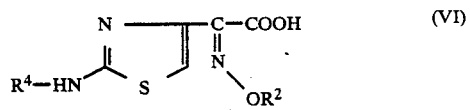

wherein $R^2$ is a straight chain, branched chain or cyclic lower alkyl, lower alkenyl or lower alkynyl group which may be substituted by a protected carboxyl group, and $R^4$ is a hydrogen atom or an amino-protecting group, to form a compound having the formula:

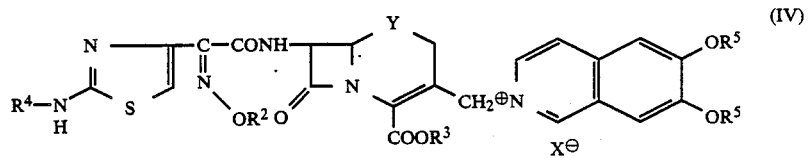

wherein $R^2$, $R^3$, $R^4$, $R^5$, $X^\ominus$ and Y are as defined above, and optionally reducing the compound of the formula IV, followed by the removal of the protecting groups.

The present invention also provides an antibacterial agent comprising an antibacterially effective amount of the compound of the formula I and a pharmaceutically acceptable carrier.

Furthermore, the present invention provides an inter-

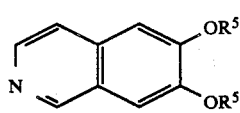

wherein $R^5$ is a hydrogen atom or a hydroxyl-protecting group, to form a compound having the formula:

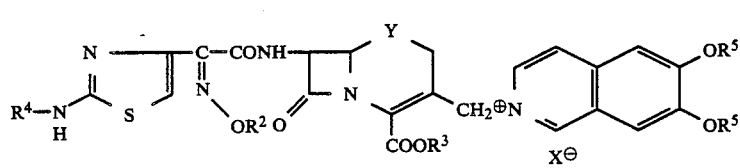

wherein $R^2$, $R^3$, $R^4$, $R^5$ and Y are as defined above, and $X^\ominus$ is an anion, and optionally reducing the compound of the formula IV, followed by the removal of the protecting groups.

Another process of the preparation of the compound of the formula I, comprises acylating a compound having the formula:

mediate having the formula:

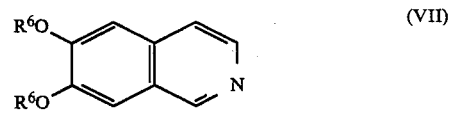

wherein $R^6$ is a hydrogen atom or an alkanoyl group or a salt thereof.

The present invention further provides a process for preparing the intermediate of the formula VII or a salt thereof, which comprises removing hydroxyl-protecting group from a compound having the formula

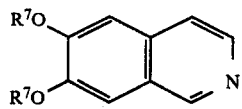 (VIII)

wherein $R^7$ is a hydroxyl-protecting group (provided that $R^7$ is not an alkanoyl group) or a salt thereof, and optionally acylating the reaction product.

DETAILED DESCRIPTION OF THE PREFERRED EMBODIMENTS

Now, the symbols and terms used in the present specification will be explained.

The substituent R in the compound of the formula I represents a straight chain or branched chain lower alkyl, lower alkenyl or lower alkynyl, or cyclic lower alkyl group, which may be substituted by a carboxyl group. The substituent $R^6$ in the compound of the formula VII represents a hydrogen atom or an alkanoyl group. The substituent $R^7$ in the compound of the formula VIII represents a hydroxyl-protecting group which can be removed by a reaction such as dealkylation, dealkylidenation, hydrolysis or catalytic reduction. Namely, $R^7$ represents a lower alkyl group, an aralkyl group, an aroyl group or a lower alkoxycarbonyl group, or two $R^7$ may together form an orthoester, a cyclic acetal group, a cyclic ketal group or a carbonate group. The straight chain or branched chain lower alkyl group includes alkyl groups having from 1 to 6 carbon atoms, such as methyl, ethyl, n-propyl, isopropyl, n-butyl, isobutyl, sec-butyl, t-butyl, n-pentyl and n-hexyl. Particularly preferred are, for example, methyl, ethyl, n-propyl and isopropyl. The lower alkenyl group includes alkenyl groups having from 2 to 6 carbon atoms such as vinyl, allyl, isopropenyl, 1,1-dimethylallyl, 2-butenyl and 3-butenyl. The lower alkynyl group includes alkynyl groups having from 2 to 3 carbon atoms, such as ethynyl and 2-propynyl. The cyclic lower alkyl group includes cyclopropyl, cyclobutyl, cyclopentyl and cyclohexyl. As preferred examples of the substituent R containing a carboxyl group as a substituent, there may be mentioned carboxymethyl, 1-carboxy-1-methylethyl, 1-carboxy-1-cyclopropyl, 1-carboxy-1-cyclobutyl, 1-carboxy-1-cyclopentyl, 1-carboxyvinyl, 1-carboxyallyl, 2-carboxyallyl, 1-carboxymethylvinyl, 2-carboxyethynyl, 1-carboxy-2-propynyl and 3-carboxy-2-propynyl.

The aralkyl group includes benzyl, p-methoxybenzyl and phenetyl. The alkanoyl group includes an acetyl, propyonyl and butyryl. Particularly preferred is acetyl. The aroyl group includes a benzoyl and toluoyl group. The lower alkoxycarbonyl group may be an alkoxycarbonyl group having from 2 to 5 carbon atoms such as methoxycarboyl, ethoxycarbonyl, propoxycarbonyl, isopropoxycarbonyl, butoxycarbonyl or isobutoxycarbonyl. Particularly preferred are methoxycarbonyl and ethoxycarbonyl. The orthoester includes an alkoxyalkylydene group such as methoxymethyliden and ethoxyethylidene. The cyclic acetal includes methylene acetal, ethylene acetal and benzylidene acetal. The cyclic ketal may be, for example, isopropylidene ketal.

6,7-Dihydroxyisoquinoline and 6,7-diacetoxyisoquinoline are novel compounds not disclosed in literatures. Cephalosporin derivatives having a 6,7-dihydroxyisoquinoliniomethyl group or a 6,7-diacetoxyisoquinoliniomethyl group at the 3-position of the cephem nucleus have not been previously synthesized.

The compound of the formula I of the present invention having a 6,7-dihydroxyisoquinoliniomethyl group at the 3-position of a cephalosporin nucleus, has the following feature.

In this specification, the structure of the 6,7-dihydroxyisoquinolinio group in the formula I is represented by the following formula A for the convenience sake.

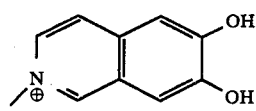 (A)

However, the formula A has a tautomer attributable to the 6,7-dihydroxyisoquinoline nucleus and may also be represented by the formula A'.

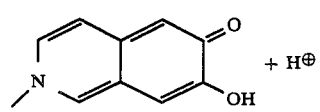 (A')

Namely, the compounds of the formulas A and A' are in an equilibrium condition of tautomerism whereby they are tautomerizable to each other depending upon the state of the compounds (e.g. solid or liquid), the type of the solvent, the nature of the solution, the temperature, etc. Thus, both of such tautomers are within the scope of the present invention.

Further, the moiety

in the oxyimino group in the formula I, includes a syn-isomer

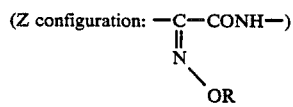

and an anti-isomer

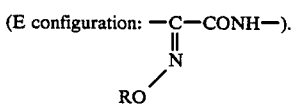

Generally, the syn-isomer exhibits superior antibacterial activities. In this specification, the OR group represents the syn-isomer in all cases. The nomenclature for E and Z configurations is described in Journal of the American Chemical Society, Vol. 90, p 509 (1968).

The compounds of the formula I may be converted to non-toxic salts or physiologically hydrolyzable non-toxic esters thereof by usual methods. The non-toxic salts of the compounds of the formula I mean pharmaceutically acceptable usual salts. Namely, salts may be formed at the carboxylic group at the 4-position of the cephem nucleus, at the carboxylic group which is contained in the substituent R at the 7-position of the cephem nucleus, at the 2-aminothiazol group of the 7-position of the cephem nucleus, or the quarternized isoquinoline moiety at the 3-position of the cephem nucleus. For instance, a salt of a metal such as sodium, potassium, calcium, magnesium or aluminum, a salt of an organic amine such as N,N'-dibenzylethylenediamine or procaine, a salt of an inorganic acid such as hydrochloric acid, hydrobromic acid, nitric acid, sulfuric acid or perchloric acid, a salt of an organic acid such as acetic acid, lactic acid, propionic acid, maleic acid, fumaric acid, malic acid, tartaric acid or citric acid, a salt of a sulfonic acid such as methanesulfonic acid, isethionic acid or p-toluenesulfonic acid and a salt of an amino acid such as glutamic acid, aspartic acid, lysine or arginine, may be mentioned.

The non-toxic esters of the compounds of the formula I mean pharmaceutically acceptable usual esters of the carboxyl groups thereof, e.g. a pharmaceutically acceptable usual ester of the carboxylic group at the 4-position of the cephem nucleus. For instance, an alkanoyloxymethyl group such as an acetoxymethyl group or a pivaloyloxymethyl group, an alkoxycarbonyloxyalkyl group such as a 1-(ethoxycarbonyloxy)ethyl group, a phthalidyl group, and a 5-substituted-2-oxo-1,3-dioxol-4-ylmethyl group such as a 5-methyl-2-oxo-1,3-dioxol-4-ylmethyl group, may be mentioned.

The compound of the formula VII can be converted to a salt thereof by a conventional method. The salt of the compound of the formula VII may be a salt of an inorganic acid such as hydrochloric acid, hydrobromic acid, sulfuric acid, nitric acid or perchloric acid, a salt of acetic acid, a salt of an organic sulfonic acid such as methanesulfonic acid or p-toluenesulfonic acid, or a salt of a hydrate thereof. Further, the salt may be suspended or dissolved in water, and neutralized with an alkali metal hydrogencarbonate such as sodium hydrogencarbonate, an alkali metal carbonate such as potassium carbonate, an alkali metal hydroxide such as sodium hydroxide or an aqueous ammonia to form a free compound.

Now, the processes for the preparation of the compounds of the present invention will be described.

The compound of the formula I may be prepared by either one of the following processes A and B.

Process A

The compound of the formula I of the present invention can be prepared by reacting a compound having the formula:

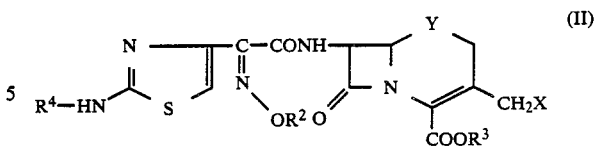

wherein $R^2$ is a straight chain, branched chain or cyclic lower alkyl, lower alkenyl or lower alkynyl group which may be substituted by a protected carboxyl group, $R^3$ is a hydrogen atom or a carboxyl-protecting group, $R^4$ is a hydrogen atom or an amino-protecting group, X is a leaving group, and Y is S or SO, or a salt thereof, with an amine having the formula:

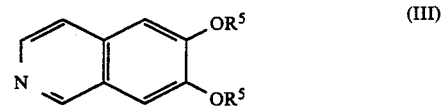

wherein $R^5$ is a hydrogen atom or a hydroxyl-protecting group, to form a compound having the formula:

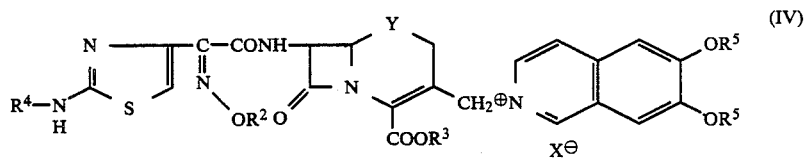

wherein $R^2$, $R^3$, $R^4$, $R^5$ and Y are as defined above, and $X^\ominus$ is an anion, and optionally reducing the compound of the formula IV, followed by the removal of the protecting groups.

The substituent X in the formula II represents a leaving group. Specifically, there may be mentioned a halogen atom such as chlorine, bromine or iodine, an acetoxy group, a carbamoyloxy group, a trifluoromethanesulfonyloxy group and a p-toluenesulfonyloxy group. Particularly preferred is a bromine atom, an iodine atom or an acetoxy group.

The 6,7-dihydroxyisoquinoline and 6,7-diacetoxyisoquinoline represented by the formula III, are novel compounds, and the hydroxyl groups may be protected.

Process B

The compound of the formula I of the present invention can also be prepared by acylating a compound having the formula:

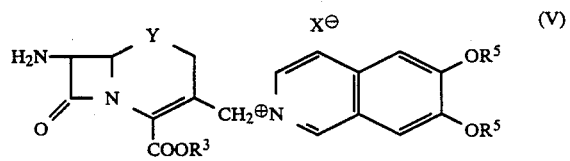

wherein $R^3$ is a hydrogen atom or a carboxyl-protecting group, $R^5$ is a hydrogen atom or a hydroxyl-protecting group, $X^\ominus$ is an anion, and Y is S or SO, or a salt thereof, with a reactive derivative of a carboxylic acid having the formula:

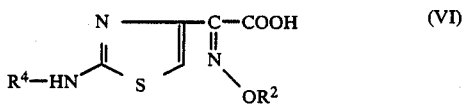 (VI)

wherein $R^2$ is a straight chain, branched chain or cyclic lower alkyl, lower alkenyl or lower alkynyl group which may be substituted by a protected carboxyl group, and $R^4$ is a hydrogen atom or an amino-protecting group, to form a compound having the formula:

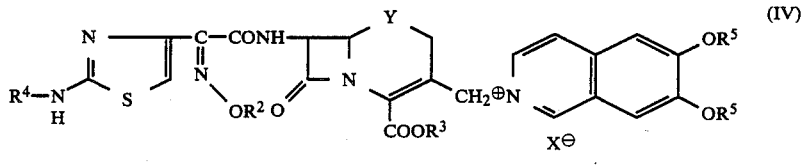 (IV)

wherein $R^2$, $R^3$, $R^4$, $R^5$, $X^\ominus$ and Y are as defined above, and optionally reducing the compound of the formula IV, followed by the removal of the protecting groups.

Further, a compound of the present invention wherein $R^1$ is an acetyl group may be prepared by conducting a substitution reaction between 6,7-diacetoxyisoquinoline of the formula III wherein $R^5$ is an acetyl group or its salt and a compound of the formula II or its salt, or acylating a 7-amino-3-(6,7-diacetoxyisoquinolinio)methyl-3-cephem-4-carboxylic acid derivative of the formula V wherein $R^5$ is an acetyl group or its salt, with a compound of the formula VI or its reactive derivative to lead it to a compound of the formula IV, and optionally reducing the compound of the formula IV and/or removing the protecting groups. Furthermore, it may also be produced by selectively acetylating a compound of the formula I or IV wherein $R^1$ or $R^5$ is an hydrogen atom under suitable conditions, and optionally reducing the formula IV and I or removing the protecting groups.

As the hydroxyl-protecting group, there may be mentioned, for example, 2-methoxyethoxymethyl, methoxymethyl, methylthiomethyl, tetrahydropyranyl, phenacyl, isopropyl, t-butyl, benzyl, 4-nitrobenzyl, acetyl, 2,2,2-trichloroethoxycarbonyl, benzyloxycarbonyl, trimethylsilyl, t-butyldimethylsilyl, an orthoester such as methoxymethylidene and methoxyethylidene, a cyclic acetal such as methylene acetal, benzylidene acetal or ethylene acetal, and a cyclic ketal such as isopropylidene ketal which are formed by the combination of protecting groups each other, a cyclic ketal such as isopropylidene ketal, or a cyclic carbonate.

Now, processes A and B for the preparation of the compounds of the formula I of the present invention, will be described in detail.

Process A

The reaction of the compound of the formula II with the 6,7-di-substituted isoquinoline of the formula III, may be conducted in an organic solvent such as methylene chloride, chloroform, ethyl ether, ethyl acetate, butyl acetate, tetrahydrofuran, acetonitrile, N,N-dimethylformamide or dimethylsulfoxide, or in a mixture of such solvents. The di-substituted isoquinoline of the formula III may be employed in the form of its acid addition salt such as hydrochloride, hydrobromide, sulfate, nitrate, formate or acetate. In such a case, this reaction is conducted in the presence of an acid-absorbing agent such as triethylamine, diisopropylethylamine, N,N-dimethylaniline or N-methylmorpholine in an amount sufficient for neutralization. Further, the di-substituted isoquinoline of the formula III may be employed in a form silylated with a silylating agent such as N,O-bi(strimethylsilyl)acetoamide. The reaction is conducted by using from 1 to 2 mols of the di-substituted isoquinoline of the formula III relative to 1 mol of the compound of the formula II. The reaction temperature and the reaction time are from 0° to 40° C. and from 0.5 to 5 hours, respectively.

The reaction of a compound of the formula II wherein X is an acetoxy group, with the di-substituted isoquinoline of the formula III, may be conducted in a solvent such as water, a phosphoric acid buffer solution, acetone, acetonitrile, methanol, ethanol, tetrahydrofuran, dioxane, N,N-dimethylformamide or dimethylsulfoxide, or in a mixture of such solvents. The reaction is preferably conducted under a neutral condition. The reaction temperature is from room temperature to 90° C., and the reaction time is from 1 to 10 hours. The reaction is facilitated by conducting it in the presence of an iodide such as sodium iodide or potassium iodide, or a thiocyanate such as sodium thiocyanate or potassium thiocyanate.

The sulfoxide group of the ammonio compound of the formula IV wherein Y is SO, can be reduced in accordance with a method described in e.g. the Journal of Organic Chemistry, Vol. 35, p 2430 (1974). Namely, the ammonio compound of the formula IV wherein Y is SO, can be reduced by reacting it with acetyl chloride in acetone as a solvent in the presence of sodium iodide or potassium iodide by a dropwise addition of acetyl chloride at a temperature of from −40° to 0° C. for from 1 to 5 hours, or by reacting the compound of the formula IV with phosphorus trichloride in a solvent such as N,N-dimethylformamide by a drowside addition of phosphorus trichloride at a temperature of from −40° to 0° C. for from 1 to 5 hours. The reaction is conducted by using from 3.5 to 10 mols of the iodide and from 1.5 to 5 mols of acetyl chloride or from 2 to 6 mols or phosphorus trichloride relative to 1 mol of the compound of the formula IV.

The compound of the formula I of the present invention may be prepared, if necessary, by removing the protecting groups from the compound of the formula IV wherein Y is S. The introduction and removal of the protecting groups may be conducted by employing a suitable method selected, for instance, from those described in Protective Groups in Organic Synthesis (1981) written by T. W. Greene.

As the protecting groups for the carboxyl, amino and hydroxyl groups in the above formulas, protecting groups which are commonly employed in the field of β-lactam synthesis, may suitably be selected for use. As the carboxyl-protecting group, there may be mentioned t-butyl, 2,2,2-trichloroethyl, acetoxymethyl, propionyloxymethyl, pivaloyloxymethyl, 1-acetoxyethyl, 1-propionyloxyethyl, 1-(ethoxycarbonyloxy)ethyl, phthalidyl, benzyl, 4-methoxybenzyl, 3,4-dimethoxybenzyl, 4-nitrobenzyl, benzhydryl, bis(4-methoxyphenyl)methyl, 5-methyl-2-oxo-1,3-dioxol-4-ylmethyl, trimethylsilyl and t-butyldimethylsilyl. Particularly preferred are benzhydryl, t-butyl and silyl.

As the amino-protecting group, there may be mentioned, for example, trityl, formyl, chloroacetyl, trifluoroacetyl, t-butoxycarbonyl, trimethysilyl and t-butyldimethylsilyl. For instance, the removal of a protecting group such as trityl, formyl, t-butoxycarbonyl, benzhydryl, t-butyl or 2-methoxyethoxymethyl, may be conducted with an inorganic or organic acid such as hydrochloric acid, formic acid, trifluoroacetic acid, benzenesulfonic acid or p-toluenesulfonic acid. Trifluoroacetic acid is particularly preferred.

When trifluoroacetic acid is used as the acid, the reaction can be facilitated by an addition of anisole, and side reactions can be thereby suppressed.

The reaction may be conducted in a solvent which is inert to the reaction, such as water, methylene chloride, chloroform, ethylene chloride or benzene, or in a mixture of such solvents. The reaction temperature and time are suitably selected depending upon the chemical properties of the compound of the formula IV and the compound of the formula I of the present invention and the type of the protecting group to be removed. The reaction is preferably conducted under a condition ranging from an ice-cooling condition to a slightly heated condition.

The compound of the formula I of the present invention wherein $R^1$ is a hydrogen atom can be prepared in accordance with a method disclosed in Japanese Unexamined Patent Publication No. 200393/1982 (Eur. Pat. Appln., No. 66373 (1982); Chem. Abstr., 98-197884u (1983), or is prepared by hydrolyzing with an alkali or by treating with acylase the compound of the present invention of the formula I wherein $R^1$ is an acetyl group.

The starting compound of the formula II for process A may be prepared in the following manner. The compound of the formula II wherein Y is S can be prepared by reacting benzhydryl 7-amino-3-chloromethyl-3-cephem-4-carboxylate (synthesized in accordance with e.g. Japanese Unexamined Patent Publications No. 76089/1975 and No. 86187/1981 or The Journal of Antibiotics 38, 1738 (1985)), 7-aminocephalosporanic acid or its ester, with a carboxylic acid of the formula VI or its reactive derivative (such as its acid halide, mixed acid anhydride, activated ester, etc.).

A compound of the formula II wherein Y is SO can be prepared by oxidizing a compound of the formula II in accordance with Journal of Organic Chemistry, 35, 2430, (1970) wherein Y is S with a stoichiometric amount of m-chloroperbenzoic acid in an organic solvent inert to the reaction such as methylene chloride, ethylene chloride or chloroform, under cooling with ice.

The compound of the formula II wherein X is an iodine atom can be prepared by reacting the compound of the formula II wherein X is a chlorine atom with an iodide such as sodium iodide or potassium iodide in an organic solvent such as acetone or N,N-dimethylformamide, or in two-phase system of water and the organic solvent in the presence of an interphase transfer catalyst, under cooling with ice or at room temperature, in accordance with a method disclosed in Japanese Unexamined Patent Publication No. 27679/1976 or Synthetic Communications, Vol. 16, p 1029–1035 (1986). The compound can also be prepared by reacting the compound of the formula II wherein X is an acetoxy group with iodotrimethylsilane in a solvent such as methylene chloride, chloroform, diethyl ether, ethyl acetate, butyl acetate, tetrahydrofuran, acetonitrile, N,N-dimethylformamide or dimethylsulfoxide, or in a mixture of such solvents, in accordance with Tetrahedoron Letters, Vol, 22, p 3915 (1981). The product may be used for the subsequent reaction without or after isolation. The 6,7-disubstituted isoquinoline of the formula III can be prepared by the acid hydrolysis of 6,7-dimethoxyisoquinoline synthesized by the method disclosed in e.g. Journal of the American Chemical Society, Vol. 79, p 3773 (1957) or J. Chem. Soc. Perkin, 1., p 2185 (1974) and p 2190 (1974), or by the catalytic reduction of a 6,7-bis(benzyloxy)isoquinoline.

2-(2-aminothiazol-4-yl)-2-substituted oxyimino acetic acid of the formula (VI) can be prepared by using 2-(2-aminothiazol-4-yl)glyoxyl acetic acid derivative or 2-(2-aminothiazol-4-yl)-2-hydroxyimono acetate derivative in accordance with a method disclosed in Chemical and Pharmaceutical Bulletin, Vol. 25, p 3115–3119 (1977) or Journal of Japanese Chemical Society, p 785–801 (1981).

Process B

The compound of the formula IV may be prepared by reacting the compound of the formula V with the carboxylic acid of the formula VI or its reactive derivative (such as its acid halide, mixed anhydride or activated ester) in a solvent inert to the reaction such as water, acetone, dioxane, acetonitrile, tetrahydrofuran, methylene chloride, chloroform, ethylene chloride, benzene, ethyl acetate, N,N-dimethylformamide or dimethylsulfoxide, or in a mixture of such solvents.

The reaction is conducted by using from 1 to 1.5 mols of the carboxylic acid of the formula VI or its reactive derivative relative to 1 mol of the compound of the formula V, and the reaction temperature is from −40° to 40° C.

When an acid halide is used as the reactive derivative of the formula VI, the reaction is preferably conducted in the presence of an acid-absorbing agent such as triethylamine, N-methylmorphorine, N,N-dimethylaniline or pyridine.

The acid halide-forming reaction is carried out by using from 1 to 10 mols, preferably from 1 to 1.5 mols of the halogenating agent such as thionyl chloride, phosphorus trichloride, phosphorus tribromide, phosphorus pentachloride, phosphorus oxychloride, oxalylchloride or phosgene, at a reaction temperature of from −40° to 100° C., preferably from −20° to 20° C. for a reaction time of 10 to 120 minutes.

The mixed acid anhydride-forming reaction is conducted by using from 1 to 1.2 mols of a chloroformate such as methyl chloroformate, ethyl chloroformate or isobutyl chloroformate in the presence of from 1 to 1.2 mols of an acid-absorbing agent such as triethylamine, N-methylmorphorine, N,N-dimethylaniline or pyridine, relative to 1 mol of the carboxylic acid of the formula VI. The reaction temperature is from −40° to 20° C., preferably from −20° to 5° C. The reaction time is from 10 to 60 minutes.

The active ester-forming reaction is conducted by using from 1 to 1.2 mols of a N-hydroxy compound (such as N-hydroxysuccinimide or 1-hydroxybenzotriazole) or a phenol compound (such as 4-nitrophenol, 2,4-dinitrophenol or trichlorophenol) and from 1 to 1.4 mols of N,N'-dicyclohexylcarbodiimide, relative to 1 mol of the carboxylic acid of the formula VI. The reaction temperature is from −10° to 50° C. The reaction time is from 0.5 to 2 hours.

When the carboxylic acid of the formula VI is used in the form of a free acid in the acylation reaction, the compound of the formula IV may be prepared in the presence of a condensation agent such as a carbodiimide such as N,N'-dicyclohexylcarbodiimide, or phosphorus oxychloride, a phosphorus oxychloride adduct of N,N-dimethylformamide. The preparation of the compound of the formula I of the present invention from the compound of the formula IV, is substantially the same as in process A.

The starting compound of the formula V in process B, may be prepared by a method disclosed in e.g. Cephalosporins and Penicillins, Academic Press, p 151–171, (1972) written by Llynn. For instance, a 7-acylamino-3-halomethyl-3-cephem-4-carboxylate derivative (Japanese Unexamined Patent Publication Nos. 72590/1983 or 154588/1983) or a 7-acylamino cephalosporanic acid derivative, is reacted with the 6,7-di-substituted isoquinoline of the formula III to obtain a compound having the formula:

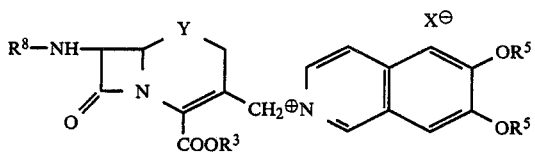

wherein $R^3$ is a hydrogen atom or a carboxyl-protecting group, $R^5$ is a hydrogen atom or a hydroxyl-protecting group, Y is S or SO, $X^\ominus$ is an anion, $R^8$ is an acyl group, followed by deacylation.

The deacylation reaction is commonly known in this field. The deacylation of the compound of the above formula wherein $R^8$ is, for example, phenylacetyl, phenoxyacetyl or aminoadipyl is conducted in accordance with a method described in Japanese Examined Patent Publication No. 20319/1974. For instance, substituent $R^8$ can be removed by reacting the compound of the above formula with phosphorus pentachloride or phosphorus oxychloride in a solvent such as benzene, toluene, ethyl acetate, methylene chloride, ethylene chloride, or in a mixture of such solvents, in the presence of an acid-absorbing agent such as N,N-dimethylaniline, pyridine, triethylamine, sodium hydrogencarbonate or potassium hydrogencarbonate at a temperature from −80° to 50° C., preferably from −65° to 0° C. for from 0.5 to 2 hours, and then treated with a lower alcohol such as methanol, ethanol or propanol, followed by hydrolysis.

Further, the removal of phenylacetyl, phenyloxyacetyl or animoadipyl can be conducted by the treatment with penicillin G acylase or fixed penicilline G acylase in water or in a mixture of water and an organic solvent such as acetone, actonitrile, methanol, ethanol or tetrahydrofuran at room temperature at a pH of from 7 to 8, preferably from 7.5 to 7.8, in accordance with a method described in Japanese Patent Application No. 291431/1986 by the present inventors. This reaction is prefereably conducted at a constant pH level by adding a base such as lithium hydroxide, sodium hydroxide, potassium hydroxide, triethylamine, tripropylamine or pyridine.

The process for producing a compound of the formula VII of the present invention will be described in detail.

The compound of the formula VII or its salt is prepared by removing the hydroxyl-protecting groups from the compound of the formula VIII or its salt, and optionally acylating the reaction product.

The removal of the hydroxyl-protecting groups can be conducted in accordance with the references mentioned with respect to the process for the compound of the formula I. As the hydroxyl-protecting group, particularly preferred is, for example, methyl, benzyl, methoxymethylidene, benzylidene, methyleneacetal, ethoxycarbonyl or carbonate which can be removed easily by acid decomposition, hydrolysis or catalytic reduction.

(1) Acid Decomposition or Hydrolysis

The compound of the formula VIII in a solution comprising from 1 to 10 times, preferably from 5 to 10 times of acetic acid and from 3 to 10 times, preferably from 5 to 10 times of hydrobromic acid, is boiled under nitrogen atmosphere at a temperature from 80° to 120° C. for from 2 to 30 hours. Then, the reaction solution was cooled and/or concentrated, and optionally acylated to obtain the compcund of the formula VII. Acid decomposition may be conducted in nonaqueous solution such as methylene chloride with aluminum chloride, or aluminum bromide alone or in the ethanethiol, or boron tribromide or boron triiodide at a reaction temperature of from −50 to 50 for from 1 to 48 hours.

(2) Catalytic Reduction

The compound of the formula VIII is dissolved in water, methanol, ethanol, propanol, isopropanol, acetic acid, an aqueous hydrochloric acid solution, an aqueous hydrobromic acid solution or an aqueous sulfuric acid solution, or in a mixture of such solutions, and catalytic reduction was conducted by using from 5 to 20%, preferably from 5 to 10% by weight of a 5–10% palladium carbon catalyst relative to the compound of the formula VIII, at a reaction temperature of from 20° to 80° C. for a reaction time of from 2 to 10 hours, optionally followed by acylation to obtain the compound of the formula VII.

The resulting product (6,7-dihyroxyisoquinoline or its salt) by the acid decompositon, hydrolysis or catalytic reduction can be used for the acylation without or after isolation.

The acylation of 6,7-dihydroxyisoquinoline or its salt is conducted, optionally in a solvent inert to the reaction such as acetic acid, trifluoroacetic acid acetone, N,N-dimethylformamide, dimethylsulfoxide or in a mixture of such solvents, by using mixed acid anhydrides, acid anhydride or acid halide in the presence of a catalytic amount or excess of a Lewis acid or an appropriate amount of acid-absorbing agent, at a reaction temperature of from 0° to 50° C. for from 0.5 to 48 hours.

After the completion of the reaction, the compound of the formula I of the present invention or its salt is isolated from the reaction mixture and purified by a conventional separation method such as extraction with a solvent, recrystallization or chromatography.

As the Lewis acid, there may be mentioned trifluoroacetic acid, methanesulfonic acid, p-toluene sulfonic acid, hydrochloric acid, sulfuric acid or boron trifluoride.

As the acid-absorbing agent, there may be mentioned an alkali metal salt such as sodium hydrogencarbonate, potassium hydrogencarbonate, sodium carbonate, potassium carbonate or magnesium hydroxide, or an organic amine such as triethylamine, ethyldiisopropyl amine, N-methylmorpholine, pyridine or N,N-dimethylaniline.

As the acid anhydride, there may be mentioned acetic anhydride, propionic anhydride or butyric anhdride.

As the acid halide, there may be mentioned acetyl chloride, propyonyl chloride or butyl chloride.

The compound of the formula VIII can be prepared in accordance with a method disclosed in Journal of the American Chemical Society Vol. 79, p 3773 (1957) and p 2190 (1974).

The in vitro antibacterial activities of the compounds of the present invention against various microorganisms, were measured by the following agar plate dilution method. One platinum loopfull of each test microorganism incubated overnight in Mueller Hinton broth, was inoculated to Mueller Hinton agar (inoculum size: $10^6$ CFU/ml). Such culture media containing various antibiotics in various concentrations were prepared. After incubation at 37° C. for 16 hours, the minimum inhibitory concentrations (MIC: μg/ml) were measured. As comparative compounds, Cefotaxime, Ceftazidime and the compounds of Reference Examples 1 to 4 were employed. The results are shown in the following table.

TABLE

| Test microorganism | Minimum Inhibitory Concentration (MIC: μg/ml) | | | | | | | |
|---|---|---|---|---|---|---|---|---|
| | Compound of Ex. 1 | Compound of Ex. 2 | Compound of Ex. 3 | Compound of Ex. 4 | Compound of Ex. 5 | Compound of Ex. 6 | Compound of Ex. 7 | Compound of Ex. 8 |
| 1. S. aureus 209P NIHJ-JC1 | 1.56 | 1.56 | 0.78 | 25 | 25 | 25 | 1.56 | 6.25 |
| *2. S. aureus JS1 | 25 | 12.5 | 12.5 | 100 | 100 | 100 | 50.0 | 50.0 |
| 3. S. aureus BB5703 | 3.12 | 6.25 | 6.25 | 50 | 50 | 50 | 6.25 | 12.5 |
| 4. S. epidermidis IAM12012 | 0.78 | 0.78 | 0.39 | 12.5 | 6.25 | 12.5 | 0.20 | 3.12 |
| 5. M. luteus ATCC9341 | 0.10 | 0.10 | 0.20 | 6.25 | 3.12 | 6.25 | 0.20 | 0.78 |
| 6. C. freundii GN346/16 | 0.78 | 0.78 | 0.39 | 1.56 | 1.56 | 1.56 | 0.78 | 0.78 |
| 7. E. coli NIHJ JC2 | 0.05 | 0.10 | 0.10 | 0.10 | 0.05 | 0.10 | 0.20 | 0.10 |
| *8. E. coli CSH2 (RK1) | <0.006 | <0.006 | 0.0125 | <0.006 | 0.0125 | 0.0125 | <0.006 | 0.0125 |
| 9. K. pneumoniae PCI-602 | <0.006 | <0.006 | <0.006 | <0.006 | <0.006 | <0.006 | <0.006 | <0.006 |
| *10. E. coli CSH(RE45) | 0.78 | 0.39 | 0.025 | 0.39 | 0.78 | 0.025 | 0.05 | 0.10 |
| *11. K. oxytoca GN10650 | 0.78 | 0.39 | 3.12 | <0.006 | 0.0125 | 0.05 | 1.56 | 0.20 |
| *12. K. pneumoniae No. 42 | 0.025 | 0.025 | 0.10 | 0.025 | 0.05 | 0.025 | <0.006 | 0.0125 |
| 13. P. vulgaris HX-19 | <0.006 | <0.006 | <0.006 | <0.006 | <0.006 | <0.006 | <0.006 | 0.025 |
| *14. P. vulgaris No. 33 | 0.10 | 0.05 | 0.10 | 0.0125 | 0.0125 | 0.0125 | 0.05 | 0.10 |
| 15. S. marcescens IAM 1184 | 0.0125 | 0.0125 | 0.0125 | 0.0125 | <0.006 | 0.0125 | <0.006 | 0.025 |
| *16. V. freundii GN346 | 25 | 50 | 50 | 50 | 50 | 50 | 50.0 | 50.0 |
| 17. E. cloacae 963 | 0.025 | 0.025 | 0.05 | 0.025 | 0.05 | 0.125 | 0.0125 | 0.025 |
| *18. E. cloacae Nek 39 | 0.10 | 0.05 | 0.10 | 0.025 | <0.006 | 0.025 | 0.20 | 0.20 |
| *19. E. coli GN5482 | 0.39 | 0.39 | 0.39 | 0.39 | 0.20 | 0.20 | 0.78 | 0.78 |
| *20. M. morganii GN5407 | 0.10 | 0.05 | 0.05 | 0.05 | 0.10 | 0.05 | 0.05 | 0.05 |
| *21. S. marcescens No. 16-2 | 3.12 | 0.78 | 1.56 | 0.20 | 0.10 | 0.10 | 1.56 | 1.56 |
| 22. Ps. aeurginosa IF03445 | 0.78 | 0.78 | 0.39 | 0.20 | 0.39 | 1.56 | 0.78 | 0.78 |
| 23. Ps. aeruginosa AK 109 | 0.78 | 0.78 | 0.78 | 0.20 | 0.39 | 0.39 | 0.78 | 0.78 |
| 24. Ps. aeruginosa AKR17 | 100 | 25 | 100 | 0.78 | 0.39 | 1.56 | 100 | 100 |
| 25. Ps. cepacia 23 | 0.78 | 0.10 | <0.006 | <0.006 | <0.006 | 0.025 | 0.10 | 0.20 |
| *26. Ps. maltophilia GN 12873 | >100 | 100 | >100 | 1.56 | 1.56 | 25 | >100 | >100 |
| 27. A. calcoaceticus No. 4 | 0.20 | 0.20 | 0.20 | 0.10 | 0.10 | 0.20 | 0.20 | 0.20 |

| Test microorganism | Minimum Inhibitory Concentration (MIC: μg/ml) | | | | | |
|---|---|---|---|---|---|---|
| | Compound of Reference Ex. 1 | Compound of Reference Ex. 2 | Compound of Reference Ex. 3 | Compound of Reference Ex. 4 | Ceftazidime | Cefotaxime |
| 1. S. aureus 209P NIHJ-JC1 | 6.25 | 0.39 | 0.78 | 12.5 | 6.25 | 1.56 |
| *2. S. aureus JS1 | 50 | 6.25 | 25.0 | 100 | 50 | 25 |
| 3. S. aureus BB5703 | 25 | 3.12 | 3.12 | 100 | 25 | 3.12 |
| 4. S. epidermidis IAM12012 | 1.56 | — | — | — | 3.12 | 0.39 |
| 5. M. luteus ATCC9341 | 0.78 | — | — | — | 1.56 | 0.05 |
| 6. C. freundii GN346/16 | 0.20 | 0.10 | 0.10 | 1.56 | 0.20 | 0.10 |
| 7. E. coli NIHJ JC2 | 0.20 | 0.025 | 0.05 | 0.78 | 0.20 | 0.05 |
| *8. E. coli CSH2 (RK1) | 0.05 | 0.025 | 0.025 | 0.39 | 0.10 | 0.05 |
| 9. K. pneumoniae PCI-602 | 0.125 | <0.006 | <0.006 | 0.20 | 0.125 | <0.006 |
| *10. E. coli CSH(RE45) | 0.10 | 1.56 | 0.39 | 0.39 | 0.10 | 0.20 |
| *11. K. oxytoca GN10650 | 0.20 | 12.5 | 3.12 | 0.39 | 0.20 | 0.78 |
| *12. K. pneumoniae No. 42 | 0.39 | 0.10 | 0.10 | 0.78 | 0.39 | 0.05 |
| 13. P. vulgaris HX-19 | 0.0125 | <0.006 | 0.0125 | 0.0125 | 0.025 | <0.006 |
| *14. P. vulgaris No. 33 | 0.10 | 0.10 | 0.05 | 0.10 | 0.05 | 0.025 |
| 15. S. marcescens IAM 1184 | 0.05 | 0.025 | 0.025 | 0.20 | 0.025 | 0.05 |
| *16. V. freundii GN346 | 50 | 6.25 | 12.5 | >100 | 25 | 25 |
| 17. E. cloacae 963 | 0.20 | 0.025 | 0.05 | 0.78 | 0.20 | 0.10 |
| *18. E. cloacae Nek 39 | 1.56 | 0.78 | 0.78 | 12.5 | 1.56 | 3.12 |
| *19. E. coli GN5482 | 0.78 | 0.20 | 0.39 | 6.25 | 3.12 | 0.39 |
| *20. M. morganii GN5407 | 0.05 | 0.025 | 0.025 | 0.10 | 0.10 | 0.05 |
| *21. S. marcescens No. 16-2 | 1.56 | 3.12 | 3.12 | 6.25 | 1.56 | 25 |
| 22. Ps. aeruginosa IF03445 | 3.12 | 3.12 | 12.5 | 6.25 | 0.39 | 3.12 |
| 23. Ps. aeruginosa AK 109 | 3.12 | 3.12 | 50 | 6.25 | 1.56 | 12.5 |
| 24. Ps. aeruginosa AKR17 | 100 | >100 | >100 | >100 | >100 | >100 |
| 25. Ps. cepacia 23 | 6.25 | 6.25 | 6.25 | 1.56 | 1.56 | 6.25 |
| *26. Ps. maltophilia GN 12873 | 12.5 | >100 | >100 | 50 | 100 | >100 |

TABLE-continued

| | | | | | | |
|---|---|---|---|---|---|---|
| 27. *A. calcoaceticus* No. 4 | 25 | 12.5 | 25 | 25 | 6.25 | 25 |

*β-Lactamase-producing strains

Thus, the compounds of the present invention exhibit strong antibacterial activities against sensitive and resistant Gram-negative bacteria particularly glucose non-fermentative Gram-negative rods, such as *Pseudomonas aeruginosa, Pseudomonas cepacia, Pseudomonas maltophilia,* and *Acinetobacter calcoaceticus.*

Further, with respect to the compound of Example 4, the β-lactamase inducibility was measured by *Enterobacter cloacae* GN 5797, whereby no substantial β-lactamase-inducing activity was observed. The assay method for induction of β-lactamase by β-latam antibiotics was as follows:

The test organism, *Enterobacter cloacae* GN 5797, was grown overnight in Mueller Hinton broth (DIfco Laboratories, Detroit, Mich.) at 37° C. The culture was diluted 10-fold into 20 ml of the flesh medium and incubated with shaking at 37° C. After 2 hours of incubation, antibiotics were added to final concentrations of 50 μg/ml, 10 μg/ml and 1 μg/ml, and the incubation was continued. At 1 hour intervals after the addition of antibiotic, 3 ml of sample was taken, and immediately added with 0.1 ml of 50 mM sodium azide. The cells were harvested and washed with 50 mM phosphate buffer (pH 7.0). The cells were suspended in 5 ml of 50 mM phosphate buffer and disrupted with a sonicater in an ice-water bath. The broken cells were centrifuged at 16,500 G for 40 minutes at 4° C., and the resulting supernatant fluid was used as the crude enzyme. β-Lactamase activity was determined by a spectrophotometric method (Antmicrob. Agents Chemother. 17, 355–358, 1980) with cephaloridine as substrate. The concentration of protein was determined by the method of Lowry (J. Biol. Chem. 193, 265–275, 1951).

| Test compound | Concentration (μg/ml) | Incubation time (hr) | Specific activity (unit/mg protein) |
|---|---|---|---|
| Compound of Example 4 | 10 | 3 | 0.064 |
| Cefoxitin | 10 | 3 | 0.238 |

(Substrate: 100 μM of cephaloridine)

Thus, the compounds of the formula I and non-toxic salts and physiologically hydrolyzable non-toxic esters thereof are useful as antibacterial agents.

The compounds of the present invention may be mixed with a carrier of solid or liquid excipient, and may be used in the form of a pharmaceutical formulation suitable for parenteral administration, oral administration or external administration. As the pharmaceutical formulations, there may be mentioned liquid formulations such as injection solutions, syrups and emulsions, solid formulations such as tablets, capsules and granules and formulations for external application such as ointments and suppositories. Further, these formulations may contain commonly employed additives such as assisting agents, stabilizers, wetting agents, emulsifying agents, absorption-promoting agents or surfactants. As such additives, distilled water for injection, a Ringer solution, glucose, sucrose syrup, gelatin, edible oil, coconut oil, ethylene glycol, sucrose, corn starch, magnesium stearate and talc, may be mentioned.

Further, the compounds of the present invention can be used as antibacterial agents for the treatment of infections diseases caused by Gram-negative bacteria including glucose non-fermentative Gram-negative rods such as *Pseudomonas aeruginosa, Pseudomonas cepacia, Pseudomonas maltophilia,* and *Acinetobacter calcoaceticus.* The dose may vary depending upon the age, sex and condition of the patient, and is usually within a range of from 1 to 100 mg/kg per day. It is preferred to administer a daily dose of from 1 to 50 mg/kg in 2 to 5 times.

Now, the present invention will be described in further detail with reference to Examples. However, it should be understood that the present invention is by no means restricted to these specific Examples.

EXAMPLE 1

Preparation of 7-[2-(2-aminothiazol-4-yl)-2-methoxyiminoacetoamido]-3-(6,7-dihydroxyisoquinolinio)-methyl-3-cephem-4-carboxylate (syn-isomer)

(A) 6.35 ml (68 mmol) of phosphorus oxychloride was added to 20 ml of dry ethyl acetate. 5.28 ml (68 mmol) of N,N-dimethylformamide was dropwise added thereto at 0° C., and the mixture was stirred at the same temperature for 15 minutes. To this solution, 180 ml of dry methylene chloride was added. 25.2 g (57 mmol) of 2-methoxyimino-2-(2-tritylaminothiazol-4-yl)acetic acid (syn-isomer) was added thereto at 0° C., and the mixture was stirred for 30 minutes. Then, to this solution, 23.6 g (57 mmol) of benzhydryl 7-amino-3-chloromethyl-3-cephem-4-carboxylate was added, and the mixture was stirred at 0° C. for 2 hours. The reaction solution was adjusted to pH 7.0, and insoluble substances were filtered off. The filtrate was washed sequentially with a 5% sodium hydrogen carbonate aqueous solution and a saturated sodium chloride aqueous solution, then dried over anhydrous sodium sulfate and concentrated under reduced pressure to obtain 44.5 g (yield: 99%) of benzhydryl 3-chloromethyl-7-[2-methoxyimino-2-(2-tritylaminothiazol-4-yl)acetamido]-3-cephem-4-carboxylate (syn-isomer).

IR(KBr) cm$^{-1}$: 1780, 1720, 1670, 1520

NMR(DMSO-d$_6$) δ: 3.67(2H, br s), 3.85(3H, s), 4.45(2H, br s), 5.25(1H, d, J=4.5 Hz), 5.80(1H, m), 6.77(1H, s), 7.00(1H, s), 7.10–7.70(25H, m), 8.80(1H, m), 9.60(1H, m)

(B) 2.5 g (2.97 mmol) of the compound obtained in the above step (A), was dissolved in 25 ml of benzene, and 640 mg (3.27 mmol) of m-chloroperbenzoic acid was added under cooling with ice. The mixture was stirred at room temperature for 1 hour. The reaction solution was poured into ice water, and extracted with ethyl acetate. The extract was washed with a 5% acidic sodium sulfite aqueous solution and a saturated sodium chloride aqueous solution, then dried over anhydrous sodium sulfate and concentrated under reduced pressure to obtain powdery benzhydryl 3-chloromethyl-7-[2-methoxyimino-2-(2-tritylaminothiazol-4-yl)acetamido]-3-cephem-4-carboxylate 1-oxide (syn-isomer).

NMR(CDCl$_3$) δ: 3.25 and 3.70(2H, ABq, J=18 Hz), 4.03(3H, s), 4.13 and 4.70(2H, ABq, J=12 Hz), 4.47(1H, d, J=5 Hz), 6.07(1H, dd, J=5 and 9 Hz), 6.67(1H, s), 6.92(1H, s), 7.30(27H, m)

(C) The compound obtained in the above step (B) was dissolved in 50 ml of acetone, and 670 mg (4.47 mmol) of sodium iodide was added. The mixture was stirred at room temperature for 30 minutes. The reaction solution was poured into ice water, and extracted with ethyl acetate. The extract was washed with a 5% sodium thiosulfate aqueous solution, water and a saturated sodium chloride aqueous solution, then dried over anhydrous sodium sulfate and concentrated under reduced pressure to obtain powdery benzhydryl 3-iodomethyl-7-[2-methoxyimino-2-(2-tritylaminothiazol-4-yl)acetamido]-3-cephem-4-carboxylate 1-oxide (syn-isomer).

IR(KBr) cm$^{-1}$: 1790, 1720, 1680, 1510, 1370, 1290, 1230, 1160, 1040

NMR(CDCl$_3$) δ: 3.40 and 3.68(2H, ABq, J=18 Hz), 4.03(3H, s), 4.48(1H, d, J=5 Hz), 6.00(1H, dd, J=5 and 9 Hz), 6.67(1H, s), 6.95(1H, s), 7.30(27H, m)

(D) 1.0 g (1.1 mmol) of the compound obtained in the above step (C) and 300 mg (1.15 mmol) of 6,7-dihydroxyisoquinoline hydrobromide monohydrate, were dissolved in 5 ml of dry N,N-dimethylformamide, and 0.17 ml (1.2 mmol) of triethylamine was dropwise added thereto at room temperature. The mixture was stirred at the same temperature for 2 hours. The reaction solution was concentrated under reduced pressure, and the residue was extracted with chloroform. The organic layer was washed with a saturated sodium chloride aqueous solution, then dried over anhydrous sodium sulfate and concentrated under reduced pressure to obtain 1.0 g (yield: 85%) of benzhydryl 3-(6,7-dihyroxyisoquinolinio)methyl-7-[2-methoxyimino-2-(2-tritylaminothiazol-4-yl)acetamido]-3-cephem-4-carboxylate 1-oxide iodide (syn-isomer).

IR(KBr) cm$^{-1}$: 1800, 1730, 1670, 1630, 1520

NMR(DMSO-d$_6$) δ: 3.50–4.10(2H, m), 3.82(3H, s), 5.10(1H, m), 5.40(2H, m), 5.95(1H, m), 6.80(1H, s), 7.00(1H, s), 7.05–8.30(29H, m), 9.03(1H, s)

(E) 1.0 g (0.9 mmol) of the compound obtained in the above step (D) and 1.5 g (9.0 mmol) of potassium iodide, were suspended in 20 ml of dry acetone, and 0.32 ml (4.5 mmol) of acetyl chloride was dropwise added thereto at −20° C. Then, the mixture was stirred at −10° C. for 3 hours. The reaction solution was poured into 100 ml of a 2% sodium metabisulfite aqueous solution, and the precipitates were collected by filtration and washed with water. The precipitates were dissolved in chloroform, then washed with a saturated sodium chloride aqueous solution, dried over anhydrous sodium sulfate and concentrated under reduced pressure to obtain 1.0 g (yield: 85%) of benzhydryl 3-(6,7-dihydroxyisoquinolinio)methyl-7-[2-methoxyimino-2-(2-tritylaminothiazol-4-yl)acetamido]-3-cephem-4-carboxylate iodide (syn-isomer).

IR(KBr) cm$^{-1}$: 1790, 1730, 1680, 1530

NMR(DMSO-d$_6$) δ: 3.55(2H, m), 3.80(3H, s), 5.25(1H, d, J=4.5 Hz), 5.50(2H, m), 5.85(1H, m), 6.70(1H, s), 6.95(1H, s), 7.00–7.80(26H, m), 8.75(1H, m), 9.50(2H, m)

(F) 0.9 g (0.82 mmol) of the compound obtained in the above step (E), was dissolved in 7 ml of dry methylene chloride, and 1 ml of anisole was added thereto. Then, 7 ml of trifluoroacetic acid was dropwise added thereto at 0° C. The reaction solution was stirred at the same temperature for 2 hours, and then concentrated under reduced pressure. Ethyl ether was added to the residue, and the precipitates were collected by filtration. The precipitates were dissolved in 200 ml of water, and insoluble substances were removed by filtration. Then, the solution was subjected to reversed phase column chromatography (LC-Sorb, manufactured by Chemco Co.). The fractions containing the desired compound eluted with 4% tetrahydrofuran/water were concentrated and freeze-dried to obtain 105 mg (yield: 23%) of the above-identified compound.

MP: 180° C. (decomposed)

IR(KBr) cm$^{-1}$: 1770, 1620, 1540, 1440

NMR(DMSO-d$_6$) δ: 3.00–3.70(2H, m), 3.78(3H, s), 5.13(1H, d, J=4.5 Hz), 5.72(3H, m), 6.70(1H, s), 7.20(1H, s), 7.50(1H, s), 7.80(1H, m), 8.40(1H, m), 9.35(1H, br s), 9.50(1H, m)

EXAMPLE 2

Preparation of 7-[2-(2-aminothiazol-4-yl)-2-isopropoxyiminoacetamido]-3-(6,7-dihydroxyisoquinolinio)methyl-3-cephem-4-carboxylate (syn-isomer)

(A) 0.41 ml (4.4 mmol) of phosphorus oxychloride was added to 5 ml of ethyl acetate, and 0.35 ml (4.5 mmol) of N,N-dimethylformamide was dropwise added thereto under cooling with ice. Then, the mixture was stirred at room temperature for 15 minutes. To the solution, 20 ml of a methylene chloride solution containing 1.59 g (3.38 mmol) of 2-isopropoxyimino-2-(2-tritylaminothiazol-4-yl)acetic acid (syn-isomer) was added, and the mixture was stirred for 30 minutes. To the reaction solution, 1.4 g (3.37 mmol) of benzhydryl 7-amino-3-chloromethyl-3-cephem-4-carboxylate was added under cooling with ice, and the mixture was stirred for 2 hours. To the reaction solution, 50 ml of ethyl acetate and 20 ml of water were added, and the mixture was adjusted to pH 7.0 with a 5N sodium hydroxide aqueous solution. The organic layer was separated and washed sequentially with a 5% sodium hydrogen carbonate aqueous solution, water and a saturated sodium chloride aqueous solution. The organic layer was dried over anhydrous sodium sulfate and then concentrated under reduced pressure. The oily residue was purified by silica gel column chromatography to obtain 1.94 g (yield: 66%) of benzhydryl 3-chloromethyl-7-[2-isopropoxyimino-2-(2-tritylaminothiazol-4-yl) acetamido]-3-cephem-4-carboxylate (syn-isomer).

NMR(CDDl$_3$) δ: 1.32(6H, d, J=6 Hz), 3.55(2H, ABq, J=19 Hz), 4.40(2H, s), 4.62(1H, m), 5.07(1H, d, J=4.5 Hz), 6.00(1H, dd, J=4.5 and 9 Hz), 6.73 (1H, s), 6.97(1H, s), 7.20–7.60(25H, br, s)

(B) 1.94 g (2.2 mmol) of the compound obtained in the above step (A), was dissolved in 20 ml of benzene, and 480 mg (2.8 mmol) of m-chloroperbenzoic acid was added thereto under cooling with ice. The mixture was stirred for 1 hour. To the reaction solution, 50 ml of ethyl acetate was added, then washed sequentially with a 2% sodium metabisulfite aqueous solution and a saturated sodium chloride aqueous solution, dried over anhydrous sodium sulfate and concentrated under reduced pressure to obtain 2.0 g (yield: 100%) of benzhydryl 3-chloromethyl-7-[2-isopropoxyimino-2-(2-tritylaminothiazol-4-yl)acetamido]-3-cephem-4-carboxylate 1-oxide (syn-isomer).

NMR(DMSO-d$_6$) δ: 1.25(6H, m), 5.09(1H, d, J=4.5 Hz), 5.93(1H, m), 6.79(1H, s), 7.00(1H, s), 7.10–7.70 (25H, br s), 8.60(1H, d, J=9 Hz), 8.73(1H, br s)

(C) 7.0 g (7.9 mmol) of the compound obtained in the above step (B), was dissolved in 130 ml of dry acetone, and 2.4 g (16 mmol) of sodium iodide was added thereto. The mixture was stirred at 0° C. for 30 minutes. The reaction solution was concentrated under reduced pressure, and the residue was extracted with ethyl acetate. The organic layer was washed with a saturated sodium chloride aqueous solution, then dried over anhydrous sodium sulfate and concentrated under reduced pressure. The residue was purified by silica gel column chromatography (20% ethyl acetate/hexane) to obtain 5.4 g (yield: 70%) of benzhydryl 3-iodomethyl-7-[2-isopropoxyimino-2-(2-tritylaminothiazol-4-yl)acetamido]-3-cephem-4-carboxylate 1-oxide (syn-isomer).

IR(KBr) cm$^{-1}$: 1800, 1730, 1680, 1520

NMR(DMSO-d$_6$) δ: 1.23(6H, d, J=6 Hz), 3.90(2H, br s), 4.10–4.60(3H, m), 5.05(1H, d, J=4.5 Hz), 5.85 (1H, dd, J=4.5 and 9 Hz), 6.75(1H, s), 6.97(1H, s), 7.00–7.60(25H, m), 8.50(1H, d, J=9 Hz), 8.70(1H, br s)

(D) 2.1 g (yield: 84%) of benzhydryl 3-(6,7-dihydroxyisoquinolinio)methyl-7-[2-isopropoxyimino-2-(2-tritylaminothiazol-4-yl)acetamido]-3-cephem-4-carboxylate 1-oxide iodide (syn-isomer) was obtained as a foamy substance from 2.1 g (2.0 mmol) of the compound obtained in the above step (C) and 600 mg (2.3 mmol) of 6,7-dihydroxyisoquinoline hydrobromide monohydrate in the same manner as in Example 1(D).

IR(KBr) cm$^{-1}$: 1800, 1730, 1660, 1630, 1520

NMR(DMSO-d$_6$) δ: 1.20(6H, d, J=6 Hz), 3.60–4.10(2H, m), 4.31(1H, m), 5.13(1H, m), 5.20–5.70(2H, m), 5.97(1H, m), 6.77(1H, m), 7.00(1H, m), 7.00–8.20(29H, m), 8.70(2H, m), 9.03(1H, br s)

(E) 2.0 g (yield: 96%) of benzhydryl 3-(6,7-dihydroxyisoquinolinio)methyl-7-[2-isopropoxyimino-2-(2-tritylaminothiazol-4-yl)acetamido]-3-cephem-4-carboxylate iodide (syn-isomer) was obtained from 2.1 g (1.7 mmol) of the compound obtained in the above step (D) in the same manner as in Example 1(E).

NMR(DMSO-d$_6$) δ: 1.20(6H, d, J=6 Hz), 3.60(2H, m) 4.20(1H, m), 5.27(1H, d, J=4.5 Hz), 5.40–5.80(2H, m), 5.90(1H, m), 6.73(1H, m), 6.92(1H, m), 7.00–7.80(26H, m), 8.00–8.60(4H, m), 9.50–9.70(2H, m)

(F) 220 mg (yield: 23%) of the above identified compound was obtained from 2.0 g (1.7 mmol) of the compound obtained in the above step (E) in the same manner as in Example 1(F).

Mp: 180° C. (decomposed)

IR(KBr) cm$^{-1}$: 1780, 1670, 1620, 1530

NMR(DMSO-d$_6$)δ: 1.15(6H, d, J=6 Hz), 3.00–3.70(2H, m), 4.25(1H, m), 5.10(1H, d, J=4.5 Hz), 5.00–5.60(2H, m), 5.75(1H, m), 6.65(1H, s), 7.10(2H, br s), 7.47(1H, s), 7.75(1H, d, J=7 Hz), 8.35(1H, d, J=7 Hz), 9.30(1H, s), 9.40(1H, m)

EXAMPLE 3

Preparation of 7-[2-allyloxyimino-2-(2-aminothiazol-4-yl)acetamido]-3-(6,7-dihydroxyisoquinolinio)methyl-3-cephem-4-carboxylate (syn-isomer)

(A) 2.0 g (yield: 86%) of benzhydryl 7-[2-allyloxyimino-2-(2-tritylaminothiazol-4-yl)acetamido]-3-(6,7-dihydroxyisoquinolinio)methyl-3-cephem-4-carboxylate 1-oxide iodide (syn-isomer) was prepared from 2.0 g (2.0 mmol) of benzhydryl 7-[2-allyloxyimino-2-(2-tritylaminothiazol-4-yl)acetamido]-3-iodomethyl-3-cephem-4-carboxylate 1-oxide (syn-isomer) and 600 mg (2.3 mmol) of 6,7-dihydroxyisoquinoline hydrobromide monohydrate in the same manner as in Example 1(D).

IR(KBr) cm$^{-1}$: 1800, 1730, 1670, 1640, 1530

NMR(DMSO-d$_6$) δ: 3.40–4.10(2H, m), 4.55(2H, m), 5.00–5.50 (6H, m), 5.95(1H, m), 6.95(1H, s), 7.00 (1H, s), 7.05–8.00 (29H, m), 8.90 (1H, br s)

(B) 2.0 g (yield: 100%) of benzhydryl 7-[2-allyloxyimino-2-(2-tritylaminothiazol-4-yl)acetamido]-3-(6,7-dihydroxyisoquinolinio)methyl-3-cephem-4-carboxylate iodide (syn-isomer) was obtained from 2.0 g (1.8 mmol) of the compound obtained in the above step (A) in the same manner as in Example 1(E).

IR(KBr) cm$^{-1}$: 1790, 1720, 1680, 1640, 1620, 1520

NMR(DMSO-d$_6$) δ: 3.60(2H, m), 4.55(2H, m), 5.00–6.00(7H, m), 6.73(1H, m), 6.92(1H, m), 7.00–7.30 (26H, m), 8.00–8.70(3H, m), 9.60(1H, m)

(C) 140 mg (yield: 13.5%) of the above identified compound was obtained from 2.0 g (1.8 mmol) of the compound obtained in the above step (B) in the same manner as in Example 1(F).

Mp: 180° C. (decomposed)

IR(KBr) cm$^{-1}$: 1780, 1670, 1620, 1540

NMR(DMSO-d$_6$) δ: 3.00–3.80(2H, m , 3.52(2H, m), 5.00–5.60 (6H, m), 5.75(1H, m), 6.67(1H, s), 6.90–7,80(4H, m), 8.30(1H, m), 9.20(1H, m), 9.55(1H, m)

EXAMPLE 4

Preparation of 7-[2-(2-aminothiazol-4-yl)-2-(1-carboxy-1-methylethoxyimino)acetamido]-3-(6,7-dihydroxyisoquinolinio)-methyl-3-cephem-4-carboxylate (syn-isomer)

(A) 28 g (41 mmol) of 2-(1-benzhydryloxycarbonyl-1-methylethoxyimino)-2-(2-tritylaminothiazol-4-yl)acetic acid (syn-isomer) and 17 g (41 mmol) of benzhydryl 7-amino-3-chloromethyl-3-cephem-4-caroxylate, were dissolved in 300 ml of dry methylene chloride, and 15.6 ml (123 mmol) of N,N-dimethylaniline was added thereto. The mixture was cooled to −10° C., and 4 ml (43 mmol) of phosphorus oxychloride was dropwise added thereto. The reaction solution was stirred at room temperature for 2.5 hours, and then concentrated under reduced pressure. The residue was extracted with ethyl acetate. The organic layer was washed sequentially with 1N hydrochloric acid, a 5% sodium hydrogen carbonate aqueous solution and a saturated sodium chloride aqueous solution, then dried over anhydrous sodium sulfate and concentrated under reduced pressure to obtain 36 g (yield: 81%) of benzhydryl 3-chloromethyl-7-[2-(1-benzhydryloxycarbonyl-1-methylethoxyimino)-2-(2-tritylaminothiazol-4-yl)acetamido]-3-cephem-4-carboxylate (syn-isomer).

IR(KBr) cm$^{-1}$: 1790, 1740, 1690, 1530, 1500, 700

NMR(DMSO-d$_6$) δ: 1.45(6H, br s), 3.62(2H, m), 4.42(2H, br s), 5.25(1H, d, J=4.5 Hz), 5.82(1H, dd, J=4.5 and 9 Hz), 6.67(1H, s), 6.77(1H, s), 6.97(1H, s), 7.00 –7.70(35H, m), 8.77(1H, br s), 9.40(1H, d, J=9 Hz)

(B) 36 g (33 mmol) of the compound obtained in the above step (A), was dissolved in 360 ml of methylene chloride, and 6.0 g (35 mmol) of m-chloroperbenzoic acid was added thereto under cooling with ice. The mixture was stirred at the same temperature for 1 hour. The reaction solution was washed with a 2% sodium metabisulfite aqueous solution, and then concentrated under reduced pressure. The residue was extracted with ethyl acetate. The organic layer was washed with a saturated sodium chloride aqueous solution, then dried over anhydrous sodium sulfate and concentrated under reduced pressure to obtain 36 g (yield: 98%) of benzhydryl 3-chloromethyl-7-[2-(benzhydryloxycarbonyl-1-methylethoxyimino)-2-(2-tritylaminothiazol-4- yl)acetamido]-3-cephem-4-carboxylate 1-oxide (syn-isomer).

IR(KBr) cm$^{-1}$: 1800, 1730, 1680, 1510, 1490

NMR(DMSO-d$_6$) δ: 1.53(6H, br s), 3.85(2H, m), 4.53(2H, m), 5.10(1H, d, J=4.5 Hz), 5.97(1H, m), 6.80(1H, s), 6.87(1H, s), 7.00(1H, s), 7.10–7.70(35H, m), 8.45(1H, d, J=9 Hz), 8.77(1H, br s)

(C) 36 g (33 mmol) of the compound obtained in the above step (B), was dissolved in 500 ml of dry acetone, and 12 g (80 mmol) of sodium iodide was added thereto under cooling with ice. The mixture was stirred at the same temperature for 1 hour. The reaction solution was concentrated under reduced pressure, and the residue was extracted with ethyl acetate. The organic layer was washed sequentially with a 2% sodium metabisulfite aqueous solution and a saturated sodium chloride aqueous solution, then dried over anhydrous sodium sulfate and concentrated under reduced pressure. The residue was purified by silica gel column chromatography (20% ethyl acetate/hexane) to obtain 22.8 g (yield: 58.5%) of benzhydryl 7-[2-(1-benzhydryloxycarbonyl-1-methylethoxyimino)-2-(2-tritylaminothiazol-4-yl)acetamido]-3-iodomethyl-3-cephem-4-carboxylate 1-oxide (syn-isomer).

IR(KBr) cm$^{-1}$: 1800, 1730, 1690, 1520, 1500, 700

NMR(DMSO-d$_6$) δ: 1.53(6H, br s), 3.90(2H, br s), 4.43(2H, m), 5.07(1H, d, J=4.5 Hz), 5.92(1H, dd, J=4.5 and 9 Hz), 6.70(1H, s), 6.78(1H, s), 7.00(1H, s), 7.05–7.70(35H, m), 8.40(1H, d, J=9 Hz), 8.73(1H, br s)

(D) 2 g (1.7 mmol) of the compound obtained in the above step (C) and 580 mg (2.23 mmol) of 6,7-dihydroxyisoquinoline hydrobromide monohydrate was dissolved in 10 ml of N,N-dimethylformamide, and 0.3 ml (0.21 mmol) of triethylamine was dropwise added thereto at room temperature. The mixture was stirred for 2 hours. The reaction solution was concentrated under reduced pressure, and the residue was extracted with chloroform. The organic layer was washed with a saturated sodium chloride aqueous solution, then dried over anhydrous sodium sulfate and concentrated under reduced pressure. The residue was purified by silica gel column chromatography (5% methanol/chloroform) to obtain 1.65 g (yield: 85.5%) of benzhydryl 7-[2-(1-benzhydryloxycarbonyl-1-methylethoxyimino)-2-(2-tritylaminothiazol-4-yl)acetamido]-3-(6,7-dihydroxyisoquinolinio)methyl-3-cephem-4-carboxylate 1-oxide iodide (syn-isomer).

IR(KBr) cm$^{-}$: 1800, 1730, 1680, 1630

NMR(DMSO-d$_6$) δ: 1.50(6H, br s), 3.50–4.10(2H, m), 5.10 (1H, m), 5.60(2H, m), 6.00(1H, m), 6.70(1H, s), 6.80(2H, br s), 6.90–8.00 (39H, m), 8.05–8.60(2H, m), 8.70(1H, m)

(E) 1.65 g (1.2 mmol) of the compound obtained in the above step (D) and 2 g (12 mmol) of potassium iodide were suspended in dry acetone, and 0.53 ml (0.8 mmol) of acetyl chloride was dropwise added at −20° C. The reaction solution was stirred at −10° C. for 5 hours, and then poured into a 2% sodium metabisulfite aqueous solution. The precipitates were collected by filtration and washed with water. The precipitates were dissolved in chloroform, then washed with a saturated sodium chloride aqueous solution, dried over anhydrous sodium sulfate and concentrated under reduced pressure to obtain 1.3 g (yield: 80%) of benzhydryl 7-[2-(1-benzhydryloxycarbonyl-1-methylethoxyimino)-2-(2-tritylaminothiazol-4-yl)acetamido]-3-(6,7-dihydroxyisoquinolinio)methyl-3-cephem-4-carboxylate iodide (syn-isomer).

IR(KBr) cm$^{-1}$: 1790, 1740, 1680, 1640

NMR(DMSO-d$_6$)δ: 1.50(6H, br s), 3.53(2H, m), 5.30(1H, m), 5.50(2H, m), 5.90(1H, m), 6.67(1H, s), 6.75(2H, br s), 6.90–7.70(36H, m), 7.90–8.50(3H, m), 8.80(1H, m), 9.40(2H, m)

(F) 1.3 g (0.98 mmol) of the compound obtained in the above step (E), was dissolved in 20 ml of dry methylene chloride, and 1.3 ml of anisole was added thereto. Then, 20 ml of trifluoroacetic acid was dropwise added thereto at 0° C. The reaction solution was stirred at the same temperature for 2.5 hours, and then concentrated under reduced pressure. Ethyl ether was added to the residue, and the precipitates were collected by filtration. The precipitates were dissolved in 200 ml of water, and insoluble substances were removed by filtration. The filtrate was subjected to reversed phase column chromatography (LC-Sorb, manufactured by Chemco Co.), and the fractions containnng the desired compound eluted with 5% tetrahydrofuran/water were concentrated and freeze-dried to obtain 120 mg (yield: 20%) of the above identified compound.

Mp: 170° C. (decomposed)

IR(KBr) cm$^{-1}$: 1770, 1620, 1540, 1440, 1290, 1200

NMR(DMSO-d$_6$)δ: 1.40(6H, br s), 3.00–3.80(2H, m), 5.15(1H, d, J=5 Hz), 5.25–5.70(2H m), 5.80(1H, m), 6.70(1H, s), 7.00–7.50(3H, m), 7.80(1H, m), 8.35(1H, m), 9.35(2H, m)

EXAMPLE 5

Preparation of 7-[2-(2-aminothiazol-4-yl)-2-(1-carboxy-1-cyclopentyloxyimino)acetamido]-3-(6,7-dihydroxyisoquinolinio)methyl-3-cephem-4-carboxylate (syn-isomer)

(A) 2.12 g (3 mmol) of 2-(1-benzhydryloxycarbonyl-1-cyclopentyloxyimino)-2-(2-tritylaminothiazol-4-yl)acetic acid (syn-isomer) and 1.24 g (3 mmol) of benzhydryl 7-amino-3-chloromethyl-3-cephem-4-carboxylate were dissolved in 50 ml of methylene chloride, and 1.2 ml (9.6 mmol) of N,N-dimethylaniline was added thereto under cooling with ice. Then, 0.29 ml (3.15 mmol) of phosphorus oxychloride was dropwise added thereto and the reaction solution was stirred at the same temperature for 4 hours. To the reaction solution, 30 ml of chloroform and 30 ml of water were added. The organic layer was washed with water and a saturated sodium chloride aqueous solution, then dried over anhydrous sodium sulfate and concentrated to obtain benzhydryl 7-[2-(1-benzhydryloxycarbonyl-1-cyclopentyloxyimino)-2-(2-tritylaminothiazol-4-yl)acetamido]-3-chloromethyl-3-cephem-4-carboxylate (syn-isomer), which was used for the next reaction without purification.

(B) The compound obtained in the above step (A) was dissolved in 50 ml of methylene chloride, and 710 mg (3.3 mmol) of m-chloroperbenzoic acid (purity: 80%) was added under cooling with ice. The mixture was stirred for 20 minutes. To the reaction solution, 30 ml of methylene chloride and 40 ml of a 5% sodium hydrogen carbonate aqueous solution were added. Then, the organic layer was separated, and washed with water and a saturated sodium chloride aqueous solution. The organic layer was dried over anhydrous sodium sulfate and then concentrated to obtain benzhydryl 7-[2-(1-benzhydryloxycarbony-1-cyclopentyloxyimino)-2-(2-tritylaminothiazol-4-yl)acetamido]-3-chloromethyl-3-cephem-4-carboxylate 1-oxide (syn-isomer), which was used for the next reaction without purification.

(C) The compound obtained in the above step (B) was dissolved in 40 ml of acetone, and 990 mg (6.6 mmol) of sodium iodide was added thereto. The mixture was stirred at room temperature for 30 minutes. To the reaction solution, 120 ml of ethyl acetate and 20 ml of a 5% sodium thiosulfate aqueous solution were added and subjected to liquid separation. The organic layer was washed with water and a saturated sodium chloride aqueous solution, then dried over anhydrous sodium sulfate and concentrated. The concentrated residue was subjected to flash silica gel column chromatography (ethyl acetate/n-hexane=½) to obtain the fraction containing the desired product. The fraction was concentrated under reduced pressure, and isopropyl ether was added to the residue, whereby 2.92 g (yield from (A): 80.3%) of powdery benzhydryl 7-[2-(1-benzhydryloxycarbonyl-1-cyclopentyloxyimino)-2-(2-tritylaminothiazol-4-yl)acetamido]-3-iodomethyl-3-cephem-4-carboxylate 1-oxide (syn-isomer) was obtained.

NMR(DMSO-$d_6$)δ: 1.80(4H, m), 2.10(4H, m), 3.90(2H, m), 4.40(2H, m), 5.10(1H, d, J=5 Hz), 5.95 (1H, dd, J=5 and 9 Hz), 6.77(1H, s), 6.80 (1H, s), 7.35(35H, m), 8.50(1H, d, J=9 Hz), 8.80(1H, br s)

(D) 2.6 g (yield: 92%) of benzhydryl 7-[2-(1-benzhydryloxycarbonyl-1-cyclopentyloxyimino)-2-(2-tritylaminothiazol-4-yl)acetamido]-3-(6,7-dihydroxyisoquinolinio)methyl-3-cephem-4-carboxylate 1-oxide iodide (syn-isomer) was obtained from 2.5 g (2.1 mmol) of the compound obtained in the above step (C) and 600 mg (2.3 mmol) of 6,7-dihydroxyisoquinoline hydrobromide monohydrate in the same manner as in Example 4(D).

NMR(DMSO-$d_6$)δ: 1.50–2.30(8H, m), 3.50–4.10(2H, m), 5.15(1H, m), 5.30–5.70 (2H, m), 6.03(1H, m , 6.73(1H, s , 6.78 (1H, s), 7.00(1H, s), 7.05–8.20(39H, m), 8.40–8.90(2H, m), 9.10(1H, s)

(E) 2.5 g (yield: 97%) of benzhydryl 7-[2-(1-benzhydryloxycarbonyl-1-cyclopentyloxyimino)-2-(2-tritylaminothiazol-4-yl)acetamido]-3-(6,7-dihydroxyisoquinolinio)methyl-3-cephem-4-carboxylate iodide (syn-isomer) was obtained from 2.6 g (1.9 mmol) of the compound obtained in the above step (D) in the same manner as in Example 4(E).

IR(KBr) cm$^{-1}$: 1790, 1730, 1680, 1640, 1620

NMR(DMSO-$d_6$)δ: 1.40–2.40(8H, m), 3.60(2H, m), 5.30(1H, d, J=4.5 Hz), 5.40–5.80(2H, m), 5.93(1H, dd, J=4.5 and 9 Hz), 6.75(1H, s), 6.78(1H, s), 6.93(1H, s), 7.00–7.80(37H, m), 8.00–8.60(3H, m), 9.20–9.70(2H, m)

(F) 50 mg (yield: 4%) of the above identified compound was obtained from 2.5 g (18 mmol) of the compound obtained in the above step (E) in the same manner as in Example 4(F).

Mp: 175° C. (decomposed)

IR(KBr) cm$^{-1}$: 1770, 1670, 1630, 1540

NMR(DMSO-$d_6$)δ: 1.40–2.20(8H, m), 3.20–3.70(2H, m), 5.10(1H, d, J=4.5 Hz), 5.15–5.60(2H, m), 5.78(1H, m), 6.62(1H, s), 6.90–7.50(3H, m), 7.70(1H, m), 8.25 (1H, m), 9.00–9.40(2H, m)

EXAMPLE 6

Preparation of 7-[2-(2-aminothiazol-4-yl)-2-(1-carboxy-1-vinyloxyimino)acetamido]-3-(6,7-dihydroxyisoquinolinio)-methyl-3-cephem-4-carboxylate (syn-isomer)

(A) 6.03 g (20 mmol) of N-(1-t-butoxycarbonyl-1-vinyloxy)phthalimide was dissolved in a solution of 200 ml of methylene chloride and 10 ml of methanol, and then a mixture of 1.88 ml of 80% hydrazine hydrate and 40 ml of methanol, was dropwise added thereto. The mixture was stirred at room temperature for 1.5 hours, and insoluble substances were removed by filtration. The filtrate was washed 3 times with 8% aqueous ammonia and then with a saturated sodium chloride aqueous solution, and then dried over anhydrous sodium sulfate. The solvent was distilled off under reduced pressure. The residue was dissolved in 120 ml of methanol, and then 7.46 g (18 mmol) of 2-(2-tritylaminothiazol-4-yl)glyoxylic acid was added thereto. The mixture was stirred at room temperature for 3 hours. The precipitated crystals were collected by filtration to obtain 7.08 g (yield: 70.9%) of 2-(1-t-butoxycarbonyl-1-vinyloxyimino)-2-(2-tritylaminothiazol-4-yl)acetic acid (syn-isomer).

IR(KBr) cm$^{-1}$: 3400, 2970, 1725, 1630, 1100, 700

NMR(DMSO-$d_6$)δ: 1.45(9H, s), 5.20(1H, br s), 5.33(1H, br s), 7.05(1H, s), 7.10–7.40(15H, m), 8.82 (1H, br s)

(B) 5.06 g (9.76 mmol) of the compound obtained in the above reaction (A) and 4.05 g (9.76 mmol) of benzhydryl 7-amino-3-chloromethyl-3-cephem-4-carboxylate were dissolved in 100 ml of methylene chloride, and 5.56 ml (43.9 mmol) of N,N-dimethylaniline was added thereto under cooling with ice. Then, 1.07 ml (11.5 mmol) of phosphorus oxychloride was dropwise added thereto. The mixture was stirred at room temperature for 1 hour, then washed sequentially with 0.5N hydrochloric acid and a saturated sodium chloride aqueous solution and dried over anhydrous sodium sulfate. The solvent was distilled off under reduced pressure, and ethyl ether was added to the residue to obtain 8.7 g (yield: 96.7%) of benzhydryl 3-chloromethyl-7-[2-(1-t-butoxycarbonyl-1-vinyloxyimino)-2-(2-tritylaminothiazol-4-yl)acetamido]-3-cephem-4-carboxylate (syn-isomer).

IR(KBr) cm$^{-1}$: 3400, 2960, 1790, 1720, 1520, 1150, 700

NMR(DMSO-$d_6$)δ: 1.48(9H, s , 3.47 and 3.75(2H, ABq, J=18 Hz), 4.45(2H, br s), 5.19(1H, br s), 5.27(1H, d, J=4.5 Hz), 5.35(1H, br s), 5.77(1H, dd, J=4.5 and 7.5 Hz), 6.92(1H, s), 6.95(1H, s), 7.30(25H, m), 8.86(1H, br s), 9.79(1H, d, J=7.5 Hz)

(C) 2.0 g (2.06 mmol) of the compound obtained in the above reaction (B), was dissolved in 30 ml of methylene chloride, and 440 mg (2.55 mmol) of m-chloroperbenzoic acid was added thereto at −10° C. The mixture was stirred at the same temperature for 1 hour. The reaction solution was washed sequentially with a 2% sodium metabisulfite aqueous solution, a 5% sodium hydrogen carbonate aqueous solution and a saturated sodium chloride aqueous solution, then dried over anhydrous sodium sulfate and concentrated under reduced pressure to obtain 2.0 g (yield: 98.4%) of benzhydryl 7-[2-(1-t-butoxycarbonyl-1-vinyloxy)imino-2-(2-tritylaminothiazol-4-yl)acetamido]-3-chloromethyl-3-cephem-4-carboxylate 1-oxide (syn-isomer).

IR(KBr) cm$^{-1}$: 1800, 1730, 1690, 1640, 1530, 1370

NMR(DMSO-$d_6$)δ: 1.47(9H, s), 3.82(2H, br s), 4.52(2H, m), 5.07(1H, d, J=4.5 Hz), 5.20(1H, br s), 5.35(1H, br s), 5.80(1H, m), 6.97(1H, s), 7.00(1H, s), 7.10–7.60(25H, m), 8.80(1H, br s), 9.37(1H, d, J=10 Hz)

(D) 2.0 g (2.03 mmol) of the compound obtained in the above reaction (C), was dissolved in 40 ml of dry acetone, and 760 mg (5.07 mmol) of sodium iodide was added under cooling with ice. The mixture was stirred at the same temperature for 1 hour. The reaction solution was concentrated under reduced pressure, and the residue was extracted with ethyl acetate. The organic layer was washed sequentially with a 2% sodium metabisulfite aqueous solution and a saturated sodium chloride aqueous solution, then dried over anhydrous sodium sulfate and concentrated under reduced pressure. The residue was subjected to silica gel column chromatography (20% ethyl acetate/hexane) to obtain 1.4 g (yield: 64.0%) of benzhydryl 7-[2-(1-t-butoxycarbonyl-1-vinyloxy)imino-2-(2-tritylaminothiazol-4-yl)acetamido]-3-iodomethyl-3-cephem-4-carboxylate 1-oxide (syn-isomer).

IR(KBr) cm$^{-1}$: 1800, 1720, 1690, 1630, 1530, 1370

NMR(DMSO-d$_6$)δ: 1.47(9H, s), 3.87(2H, m), 4.45(2H, m), 5.07(1H, d, J=4.5 Hz), 5.20(1H, br s), 5.35(1H, br s), 5.80(1H, m), 6.98(1H, s), 7.01(1H, s), 7.10–7.60(25H, m), 8.83(1H, br s), 9.35(1H, d, J=9 Hz)

(E) 1.4 g (1.3 mmol) of the compound obtained in the above reaction (D) and 380 mg (1.46 mmol) of 6,7-dihydroxyisoquinoline hydrobromide monohydrate were dissolved in 7 ml of N,N-dimethylformamide, and 0.19 ml (1.37 mmol) of triethylamine was dropwise added thereto. The reaction solution was stirred at room temperature for 2 hours, and then concentrated under reduced pressure. The residue was extracted with chloroform. The organic layer was washed sequentially with water and a saturated sodium chloride aqueous solution, then dried over anhydrous sodium sulfate and concentrated under reduced pressure to obtain 1.2 g (yield: 74.6%) of benzhydryl 7-[2-(1-t-butoxycarbonyl-1-vinyloxy)imino-2-(2-tritylaminothiazol-4-yl)acetamido]-3-(6,7-dihydroxyisoquinolinio)methyl-3-cephem-4-carboxylate 1-oxide iodide (syn-isomer).

IR(KBr) cm$^{-1}$: 1800, 1720, 1670, 1640, 1530, 1450

NMR(DMSO-d$_6$)δ: 1.50(9H, s), 3.50–3.75(2H, m), 5.10(1H, d, J=4.5 Hz), 5.10–5.40(4H, m), 5.87(1H, m), 7.00(2H, s), 7.05–8.20(28H, m), 8.60–9.00(2H, m), 9.40(1H, m)

(F) 1.2 g (0.97 mmol) of the compound obtained in the above reaction (E) and 1.6 g (9.6 mmol) of potassium iodide were suspended in 30 ml of dry acetone, and 0.35 ml (4.9 mmol) of acetyl chloride was dropwise added thereto at −20° C. The reaction solution was stirred at −10° C. for 4 hours, and poured into 150 ml of a 2% sodium metabisulfite aqueous solution. The precipitates were collected by filtration and washed with water. The precipitates were dissolved in chloroform and washed with a saturated sodium chloride aqueous solution. The organic layer was dried over anhydrous sodium sulfate and then concentrated under reduced pressure to obtain 1.1 g (yield: 92.9%) of benzhydryl 7-[2-(1-t-butoxycarbonyl-1-vinyloxy)imino-2-(2-tritylaminothiazol-4-yl)acetamido]-3-(6,7-dihydroxyisoquinolinio)methyl-3-cephem-4-carboxylate iodide (syn-isomer).

IR(KBr) cm$^{-1}$: 1790, 1720, 1690, 1640, 1530, 1370

NMR(DMSO-d$_6$)δ: 1.52(9H, s , 3.40–3.70(2H, m), 5.10–5.95 (6H, m), 6.90(1H, s), 6.92(1H, s), 7.00–7.70(27H, m), 7.90–8.60(2H, m), 8.75(1H, m), 9.35(1H, m), 9.73(1H, m)

(G) 1.1 g (0.9 mmol) of the compound obtained in the above reaction (F), was dissolved in 7 ml of dry methylene chloride, and 1.1 ml of anisole was added. Then, 15 ml of trifluoroacetic acid was dropwise added at 0° C. The reaction solution was stirred at the same temperature for 2.5 hours, and then concentrated under reduced pressure. Ethyl ether was added to the residue, and the precipitates were collected by filtration. The precipitates were dissolved in 50 ml of a 10% methanol aqueous solution, and insoluble substances were removed by filtration. The filtrate was subjected to reversed phase column chromatography (LC-Sorb, manufactured by Chemco Co.), and the fractions containing the desired compounds eluted with 20% methanol/water were concentrated and freeze-dried to obtain 40 mg (yield: 7.3%) of the above identified compound.

Mp: 155° C. (decomposed)

IR(KBr) cm$^{-1}$: 1770, 1630, 1530, 1440

NMR(DMSO-d$_6$)δ: 3.10–3.80(2H, m), 5.00–5.65(5H, m), 5.80 (1H, m), 6.95(1H, s), 7.30(1H, m), 7.95 (2H, m), 8.45(1H, m), 9.25(1H, m), 9.75(1H, m)

EXAMPLE 7

Preparation of 7-[2-(2-aminothiazol-4-yl)-2-(2-propynyloxyimino)acetamido]-3-(6,7-dihydroxyisoquinolio)methyl-3-cephem-4-carboxylate (syn-isomer)

(A) The same operation as in Example 1(A), (B) and (C) was conducted by using 3.0 g (6.9 mmol) of 2-(2-propynyloxyimino)-2-(2-tritylaminothiazol-4-yl)acetic acid (syn-isomer) and 2.86 g (6.9 mmol) of benzhydryl 7-amino-3-chloromethyl-3-cephem-4-carboxylate, whereby 3.8 g (yield: 58.7%) of benzhydryl 3-iodomethyl-7-(2-(2-propynyloxyimino)-2-(2-tritylaminothiazol-4-yl)acetamido]-3-cephem-4-carboxylate 1-oxide (syn-isomer) was obtained.

IR(KBr) cm$^{-1}$:2120, 1800, 1730, 1690, 1520

NMR(DMSO-d$_6$)δ: 3.45(2H, s , 3.90(2H, br s), 4.40(2H, m), 4.70(2H, s), 5.05(1H, d, J=4.5 Hz), 5.85 (1H, dd, J=4.5 and 8 Hz), 6.85(1H, s), 6.98(1H, s), 7.10–7.70(25H, m), 8.80(1H, s), 9.00(1H, d, J=8 Hz)

(B) The same operation as in Example 1(D), (E) and (F) was conducted by using 2.0 g (2.1 mmol) of the compound obtained in the above reaction (A) and 600 mg (2.3 mmol) of 6,7-dihydroxyisoquinoline hydrobromide monohydrate, whereby 180 mg (yield: 12.6%) of the above identified compound was obtained.

Mp: 160° C. (decomposed)

IR(KBr) cm$^{-1}$: 2120, 1770, 1670, 1610, 1540

NMR(DMSO-d$_6$)δ: 3.00–3.70(3H, m), 4.65(2H, br s), 5.13(1H, d, J=4.5 Hz), 5.25–6.00(3H, m), 6.73(1H, s), 7.18(2H, br s), 7.50(1H, s), 7.80(1H, d, J=6 Hz), 8.40(1H, d, J=6 Hz), 9.33(1H, br s), 9.60(1H, m)

EXAMPLE 8

Preparation of 3-(6,7-diacetoxyisoquinolino)methyl-7-[2-(2-aminothiazol-4-yl)-2-methoxyiminoacetamido]-3-cephem-4-carboxylate (syn-isomer)

The same operation as in Example 1(D), (E) and (F) was conducted by using 2.5 g (2.7 mmol) of benzhydryl 3-iodomethyl-7-[2-methoxyimino-2-(2-tritylaminothiazol-4-yl)acetanido]-3-cephem-4-carboxylate 1-oxide (syn-isomer) obtained in Example 1(C) and 1.0 g (4.0 mmol) of 6,7-diacetoxyisoquinoline, whereby 25 mg (yield: 1.4%) of the above identified compound was obtained.

Mp: 185° C. (decomposed)

IR(KBr) cm$^{-1}$:1780, 1620, 1540, 1380, 1200

NMR(DMSO-d$_6$)δ: 2.30(3H, s), 2.50(3H, s), 3.20–3.70(2H, m), 3.80(3H, s), 4.80–5.60(3H, m), 5.73 (1H, m), 6.70(1H, s), 7.00(1H, br s), 7.15(1H, m), 7.75(2H, m), 8.27(1H, m), 9.17(1H, m), 9.53(1H, m)

EXAMPLE 9

Preparation of sodium 3-(6,7-diacetoxyvisoquinolinio)methyl-7-[2-(1-carboxylate-1-methylethoxyimino)-2-aminothiazol-4-yl)acetamido]-3-cephem-4-carboxyl (syn-isomer)

The same operation as in Example 1(D), (E) and (F) was conducted by using 2.5 g of the compound obtained in Example 4(C) and 728 mg (3.16 mmol) of 6,7-diacetoxyisoquinoline, and then the amino-protecting group and carboxyl-protecting group were removed, whereby the trifluoroacetic acid salt of the desired compound was obtained. The salt was suspended in water, and adjusted to pH 7.0 with a saturated sodium hydrogen carbonate aqueous solution. Then, insoluble substances were removed by filtration. The filtrate was subjected to reversed phase column chromatography (LC-Sorb, manufactured by Chemco Co.), and the fractions containing the desired compound eluted with 5% methanol/water were combined, were concentrated and freeze-dried to obtain 123 mg (yield: 7%) of the above identified compound.

MP: 175° C. (decomposed)
IR(KBr) cm$^{-1}$: 3400, 1765, 1595
NMR(DMSO-d$_6$)δ: 1.40(3H, br s), 1.46(3H, br s), 2.30(6H, s), 4.30–5.30(3H, m), 6.00(1H, m), 6.85(1H, s), 7.00–9.10(5H, m)

EXAMPLE 10

Preparation of 6,7-dihydroxyisoquinoline hydrobromide monohydrate (A) 73 g (0.172 mol) of 3,4-bis(benzyloxy)benzaldehyde was dissolved in 500 ml of benzene, and 25 ml (0.23 mol) of aminoacetaldehyde diethylacetal was added thereto. The mixture was stirred under reflux for 5 hours to remove the resulting water. The reaction solution was concentrated under reduced pressure to obtain a residue of 2-(N-[3,4-bis(benzyloxy)benzylidenlamino)acetaldehyde diethylacetal. This residue was dissolved in 700 ml of methanol, and 6.0 g (0.16 mol) of sodium borohydride was added thereto at room temperature. The mixture was stirred for 15 minutes. The reaction solution was concentrated under reduced pressure. The residue was dissolved in ethyl acetate, then washed with a saturated a sodium chloride aqueous solution, dried over anhydrous sodium sulfate and concentrated under reduced pressure to obtain a residue of 2-{N-[3,4-bis(benzyloxy)benzyl]amino}acetaldehyde diethylacetal. This residue was dissolved in 600 ml of dry tetrahydrofuran, and 39.8 g (0.21 mol) of p-toluenesulfonyl chloride and 59 ml (0.42 mol) of triethylamine were added. The mixture was stirred at room temperature for 17.5 hours. The reaction solution was concentrated under reduced pressure, and the residue was extracted with ethyl acetate. The organic layer was washed with a saturated sodium chloride aqueous solution, then dried over anhydrous sodium sulfate and concentrated under reduced pressure. The residue was subjected to silica gel column chromatography (10% ethyl acetate/hexane), whereby 70 g (yield: 70.7%) of 2-{N-(P-tolylsulfonyl)-N-[3,4-bis(benzyloxy)benzyl]amino}acetaldehyde diethyl acetal was obtained.

Mp: 75° C.
IR(KBr) cm$^{-1}$: 1600, 1520, 1460, 1340, 1250, 1160, 1130
NMR(DMSO-d$_6$)δ: 1.00(6H, t, J=7.5 Hz), 2.35(3H, s), 3.07(2H, d, J=6 Hz), 3.20-3.60(4H, m), 4.32(2H, s), 4.35(1H, d, J=6 Hz), 4.90 (2H, s), 5.08(2H, s), 6.60–7.80(17H, m)

(B) 22.1 g (39 mmol) of the compound obtained in the above step (A), was dissolved in 300 ml of dioxane, and 28 ml of 6N hydrochloric acid was added thereto. Then, the mixture was stirred under reflux for 5.5 hours in a nitrogen atmosphere at a dark place. The reaction solution was adjusted to pH 10.0 with a 20% sodium hydroxide aqueous solution, and then concentrated under reduced pressure. Then, the residue was extracted with ethyl acetate. The organic layer was washed with a saturated sodium chloride aqueous solution, then dried over anhydrous sodium sulfate and concentrated under reduced pressure. The residue was purified by silica gel column chromatography (2% methanol/chloroform) to obtain 8.6 g (yield: 64%) of 6,7-bis(benzyloxy)isoquinoline.

Mp: 97° C.
IR(KBr) cm$^{-1}$: 1620, 1580, 1500, 1240, 1140, 1000
NMR(DMSO-d$_6$)δ: 5.30(4H, s), 7.25–7.80(13H, m), 8.30(1H, d, J=6 Hz), 9.02(1H, s)

(C) 7.8 g (23 mmol) of the compound obtained in the above step (B) was dissolved in a mixture of 150 ml of methanol, 1.5 g of 10% palladium charcoal catalyst and 1.7 ml of 40% hydrobromic acid, and the mixture was stirred at from 50° to 60° C. for 7.5 hours under a hydrogen atmosphere. The reaction solution was filtered, and the filtrate was concentrated under reduced pressure. The residue was recrystallized from a 1N hydrobromic acid aqueous solution. The crystals formed were collected by filtration, washed with acetone and dried for 5 hours in vacuo to obtain 4.75 g (yield: 79.4%) of the above identified compound.

Mp: 205° C.
IR(KBr) cm$^{-1}$: 1630, 1610, 1520, 1480, 1430, 1300
NMR(DMSO-d$_6$)δ: 7.50(1H, s), 7.70(1H, s), 8.10(1H, ABd, J=6 Hz), 8.30(1H, ABd, J=6 Hz), 9.42(1H, s)
Elemental analysis: as C$_9$H$_7$NO$_2$.H$_2$O.HBr: Calculated (%): C, 41.56, H,3.88, N,5.39, Br,30.72. Found (%): C, 41.51, H, 3.85, N, 5.24, Br, 30.10.

EXAMPLE 11

Preparation of 6,7-dihydroxyisoquinoline hydrobromide monohydrate 1.9 g (10 mmol) of 6,7-dimethoxyisoquinoline was dissolved in a mixture of 15 ml of acetic acid and 15 ml of 40% hydrobromic acid, and the solution was stirred under reflux for 24 hours under a nitrogen atmosphere. The reaction solution was concentrated under reduced pressure. The residue was recrystallized from a 1N hydrobromic acid aqueous solution to obtain 2.3 g (yield: 88.4%) of the above identified compound. The melting point, infrared spectrum and NMR spectrum agreed to those of the compound of Example 10.

EXAMPLE 12

Preparation of 6,7-dihydroxyisoquinoline hydrobromide 63.4 g (0.28 mol) of 6,7-dimethoxyisoquinoline hydrochloride was dissolved in 630 ml of 47% hydrobromic acid, and the mixture was refluxed for 24 hours under stirring in nitrogen atmosphere. The reaction mixture was allowed to stand still under cooling with ice. The crystals formed were collected by filtration and washed with cold water and acetone. They were dried in air overnight and then dried at a temperature of from 90° to 95° C. for 6 hours to obtain 66.4 g (yield: 97.6%) of the above identified compound.

Mp: >260° C. (decomposed)
IR(KBr) cm$^{-1}$: 1630, 1610, 1520, 1480, 1430, 1300
NMR(DMSO-d$_6$)δ: 7.52(1H, s), 7.73(1H, s), 8.14(1H, d, J=7 Hz), 8.33(1H, d, J=7 Hz), 9.47(1H, s)

EXAMPLE 13

Preparation of 6,7-dihydroxyisoquinoline 9.78 g (40.4 mol) of 6,7-dihydroxyisoquinoline hydrobromide was dissolved under heating in 400 ml of water and treated with 1 g of active carbon. The filtrate thereby obtained was adjusted to pH8.0 with a 8% aqueous ammonia, and the mixture was stirred under cooling with ice. The crystals formed were collected by filtration. They were washed with water and acetone and dried to obtain 6.08 g (yield: 93.4%) of the above identified compound.

Mp: 258°-260° C.
IR(KBr) cm$^{-1}$: 1640, 1605, 1590, 1565, 1520, 1450, 1340
NMR(DMSO-d$_6$)δ: 7.13(1H, s), 7.29(1H, s), 7.48(1H, d, J=6 Hz), 8.15(1H, d, J=6 Hz), 8.91(1H, s)

EXAMPLE 14

Preparation of 6,7-diacetoxyisoquinoline 500 mg (1.9 mmol) of 6,7-dihydroxyisoquinoline hydrobromide monohydrate was suspended in 10 ml of trifluoroacetic acid, and 2.0 ml (21 mmol) of acetic anhydride was added thereto at room temperature. The mixture was stirred at the same temperature for 24 hours. The reaction solution was concentrated under reduced pressure. Water and ethyl acetate were added to the residue. Then, the aqueous solution was adjusted to pH 8.0 with a 5% sodium hydrogen carbonate aqueous solution, and extracted with ethyl acetate. The extract was washed with a saturated sodium chloride aqueous solution, then dried over anhydrous sodium sulfate and concentrated under reduced pressure to obtain 440 mg (yield: 93.4%) of the above identified compound.

IR(KBr) cm$^{-1}$: 1770, 1620, 1500, 1460, 1380, 1200
NMR(DMSO-d$_6$)δ: 2.39(6H, s), 7.85(1H, d, J=6 Hz), 7.90(1H, s), 8.05(1H, s), 8.53(1H, d, J=6 Hz), 9.30(1H, s)

REFERENCE EXAMPLE 1

Preparation of sodium 7-[2-(2-aminothiazol-4-yl)-2-(1-carboxylate-1-methylethoxyimino)acetamido]-3-isoquinoliniomethyl-3-cephem-4-carboxylate (syn-isomer)

450 mg (0.48 mmol) of 7-[2-(1-benzhydryloxycarbonyl-1-methylethoxyimino)-2-(2-tritylaminothiazol-4-yl)acetamido]cephalosporanic acid and 15 mg (0.085 mmol) of ascorbic acid were dissolved in 3 ml of acetone, and 1 ml of water, 2.88 g (19.2 mmol) of sodium iodide and 0.6 ml (50 mmol) of isoquinoline were added thereto. The mixture was stirred at from 50° to 60° C. for 5 hours. The reaction solution was extracted with chloroform, then dried over anhydrous sodium sulfate and concentrated under reduced pressure. The residue was dissolved in 5 ml of dry methylene chloride, and 0.5 ml of anisole was added. Then, 5 ml of trifluoroacetic acid was dropwise added thereto at 0° C. The mixture was stirred at the same temperature for 2 hours. The reaction solution was concentrated under reduced pressure, and ethyl ether was added to the residue. The precipitates were collected by filtration. Then, precipitates were dissolved in 100 ml of water and adjusted to pH 6.5 with a sodium hydrogen carbonate aqueous solution. Then, insoluble substances were removed by filtration. The filtrate was subjected to reversed phase column chromatography (LC-Sorb, manufactured by Chemco Co.), and the fractions containing the desired compound eluted with 5% methanol/water were concentrated and freeze-dried to obtain 15 mg (yield: 5%) of the above identified compound.

NMR(DMSO-d$_6$)δ: 1.38(6H, br s), 3.10–3.70(2H, m), 5.05 (1H, d, J=5 Hz), 5.70(1H, m), 6.65(1H, s), 7.10(2H, m), 7.90–8.60(6H, m), 9.25(1H, m)

REFERENCE EXAMPLE 2

Preparation of 7-[2-(2-aminothiazol-4-yl)-2-methoxyiminoacetamido]-3-(5-hydroxyisoquinolinio)methyl-3-cephem-4-carboxylate (syn-isomer)

500 mg (0.99 mmol) of cefotaxime formic acid salt was dissolved in a solution of 15 ml of 50% aqueous acetone, and 5.95 g (39.7 mmol) of sodium iodide, 1.43 g (9.9 mmol) of 5-hydroxyisoquinoline and 30 mg of ascorbic acid were added thereto. The mixture was stirred at 60°–65° C. for 4 hours. The reaction mixture was cooled, and 40 ml of acetone was added thereto. The mixture was subjected to silica gel column chromatography (Wakogel C-300) eluting with 10% acetone/water. The fractions containing the desired compound were combined and concentrated to about 40 ml under reduced pressure. The concentrate was charged on reversed phase column chromatography (LC-Sorb, manufactured by Chemco Co.), which was eluated with 20% methanol/water. The fractions containing the desired compound were combined, concentrated and freeze-dried to obtain 72 mg (yield: 13.4%) of the above identified compound.

MP: 195° C. (decomposed)
IR(KBr) cm$^{-1}$: 1770, 1610, 1530, 1400, 1290
NMR(DMSO-d$_6$)δ: 3.00–3.60(2H, m), 3.80(3H, s), 5.10(1H, d, J=4.5 Hz), 5.20–5.90(3H, m), 6.72(1H, s), 7.55(1H, m), 7.87(2H, m), 8.50(1H, d, J=6.0 Hz), 8.95(1H, d, J=6.0 Hz), 10.18(1H, s)

REFERENCE EXAMPLE 3

Preparation of 7-[2-(2-aminothiazol-4-yl)-2-methoxyiminoacetamido]-3-(8-hydroxyisoquinolinio)methyl-3-cephem-4-carboxylate (syn-isomer)

The same operation as in Reference Example 2 was conducted by using 500 mg (0.99 mmol) of cefotaxime formic acid salt and 1.43 g (9.9 mmol) of 8-hydroxyisoquinoline whereby 52 mg (yield: 9.7%) of the above identified compound was obtained.

MP: 185° C. (decomposed)
IR(KBr) cm$^{-1}$: 1770, 1600, 1530, 1380, 1300
NMR(DMSO-d$_6$)δ: 3.20–3.60(2H, m), 3.80(3H, s), 5.10 (1H, d, J=4.5 Hz), 5.20–5.90(3H, m), 6.63(1H, s), 7.30(1H, d, J=7.0 Hz), 7.60(1H, d, J=7.0 Hz), 8.03(1H, t, J=7.0 Hz), 8.30(1H, d, J=6.0 Hz), 8.80(1H, d, J=6.0 Hz), 10.23(1H, s)

REFERENCE EXAMPLE 4

Preparation of sodium 7-[2-(2-aminothiazol-4-yl)-2-(1-carboxylate-1-methylethoxyimino)acetamido]-3-(5-hydroxyisoquinolinio)-methyl-3-cephem-4-carboxylate (syn-isomer)

The same operation as in Reference Example 1 was conducted by using 1.0 g (1.07 mmol) of 7-[2-(1-benzhydryloxycarbonyl-1-methylethoxyimino)-2-(2-tritylaminothiazol-4-yl)acetamido]cephalosporanic (syn-isomer) and 1.55 g (10.7 mmol) of 5-hydroxyisoquinoline, whereby 46 mg (yield: 6.8%) of the above identified compound was obtained.

MP: 205° C. (decomposed)

IR(KBr) cm$^{-1}$: 1770, 1600, 1530, 1400, 1290

NMR(DMSO-d$_6$)δ: 1.40(6H, br s), 3.20–3.60(2H, m), 5.07(1H, d, J=4.5 Hz), 5.20–5.90(3H, m), 6.70(1H, s), 7.55(1H, m), 7.65(2H, m), 8.45(1H, m), 8.70(1H, m), 10.00(1H, s)

The compounds of the present invention are novel compounds not disclosed in literatures. They exhibit excellent antibacterial activities particularly against sensitive and resistant Gram-positive and Gram-negative bacteria. They have strong antibacterial activities particularly against resistant Gram-negative bacteria including *Pseudomonas aeruginosa*, excellent stability against β-lactamase and low β-lactamase inducing activity, and thus they are effective as antibacterial agents.

In particular, the compounds of the present invention having a 6,7-dihydroxyisoquinoliniomethyl group or 6,7-diacetoxyisoquinoliniomethyl group, wherein hydroxyl groups or acetoxy groups are introduced at the 6- and 7-positions of the isoquinoline nucleus of the isoquinoliniomethyl group at the 3-position, particularly the compounds of Examples 1 to 6, exhibit unexpectedly strong antibacterial activities against sensitive and resistant Gram-negative bacteria as compared with the compound wherein the isoquinoline nucleus has no substituent (the compound of Reference Example 1) and the monohydroxy substituted compounds (Reference Examples 2–4). Further, the compound of the present invention of the formula VII is also novel compound not disclosed in any literature and useful as an intermediate for the compound of the present invention.

What is claimed is:

1. A compound having the formula

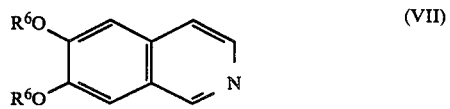

(VII)

wherein R$^6$ is a hydrogen atom or an alkanoyl group, or a salt thereof.

2. The compound according to claim 1, wherein R$^6$ is a hydrogen atom.

3. The compound according to claim 1, wherein R$^6$ is acetyl, propionyl or butyryl.

4. The compound according to claim 1, which is 6,7-dihydroxyisoquinoline or 6,7-diacetoxyisoquinoline.

* * * * *

UNITED STATES PATENT AND TRADEMARK OFFICE
CERTIFICATE OF CORRECTION

PATENT NO.    :   4,782,155

DATED         :   Nov. 1, 1988

INVENTOR(S)   :   Susumu NAKAGAWA et al.

It is certified that error appears in the above-identified patent and that said Letters Patent is hereby corrected as shown below:

On the Title Page, Item [30]:

Please add the following to the Foreign Application Priority Data:

-- Mar. 11, 1987 [JP]  Japan ....................62-55535

Mar.  9, 1987 [JP]  Japan ....................62-53845 --

Signed and Sealed this

Fourteenth Day of March, 1989

Attest:

DONALD J. QUIGG

*Attesting Officer*       *Commissioner of Patents and Trademarks*